(12) United States Patent
Kratzsch et al.

(10) Patent No.: US 7,547,535 B2
(45) Date of Patent: *Jun. 16, 2009

(54) FORMS OF SOLUBLE PYRROLOQUINOLINE QUINONE-DEPENDENT GLUCOSE DEHYDROGENASE

(75) Inventors: Peter Kratzsch, Antdorf (DE); Rainer Schmuck, Benediktbeuern (DE); Daniela Beck, Iffeldorf (DE); Zhixin Shao, Penzberg (DE); Detlef Thym, Mannheim (DE); Wolfgang-Reinhold Knappe, Ludwigshafen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 265 days.

This patent is subject to a terminal disclaimer.

(21) Appl. No.: 11/298,778

(22) Filed: Dec. 9, 2005

(65) Prior Publication Data
US 2006/0148056 A1     Jul. 6, 2006

Related U.S. Application Data

(63) Continuation of application No. 10/319,147, filed on Dec. 13, 2002, now Pat. No. 7,132,270, which is a continuation-in-part of application No. 10/082,627, filed on Oct. 29, 2001, now abandoned, which is a continuation-in-part of application No. 09/710,197, filed on Nov. 9, 2000, now abandoned.

(30) Foreign Application Priority Data

Oct. 27, 2000   (EP)   ............................... 00123512
Dec. 19, 2000   (EP)   ............................... 00127294

(51) Int. Cl.
*C12N 9/04*     (2006.01)
*C07H 21/04*    (2006.01)
(52) U.S. Cl. .......................... 435/190; 536/23.2
(58) Field of Classification Search ........... 435/189, 435/200, 7.1, 287.1, 69.1, 320.1, 325, 190; 536/22.1, 23.2
See application file for complete search history.

(56) References Cited

U.S. PATENT DOCUMENTS

| | | | |
|---|---|---|---|
| 5,484,708 A | 1/1996 | Hoenes et al. | |
| 5,997,817 A | 12/1999 | Crismore et al. | |
| 6,057,120 A | 5/2000 | Heindl et al. | |
| 6,103,509 A | 8/2000 | Sode | |
| 6,190,906 B1 | 2/2001 | Schumacher et al. | |
| 7,132,270 B2 * | 11/2006 | Kratzsch et al. | 435/190 |
| 2004/0265828 A1 | 12/2004 | Sode | |

FOREIGN PATENT DOCUMENTS

| EP | 0620283 B1 | 10/1994 |
|---|---|---|
| EP | 1 167 519 A1 | 1/2002 |
| EP | 1 176 202 A1 | 1/2002 |
| WO | 88/09373 | 12/1988 |
| WO | 92/07953 | 5/1992 |
| WO | 99/30152 | 6/1999 |
| WO | 00/61730 | 10/2000 |
| WO | 0066744 | 11/2000 |

OTHER PUBLICATIONS

Branden et al. Introduction to protein structure, Gerald Publishing Inc., New York, p. 247, 1991.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Seffernick et al. Melamine deaminase and atrazine chlorohydrolase: 98 percent identical but functionally different, J Bacteriol. Apr. 2001;183(8):2405-10.*
Database WPI, Section Ch, Week 200064, Derwent Publications Ltd., London, GB, AN 2000-665126, XP0061730.
Japanese Abstract, JP11243949, Takeshima Seiji et al. (1999).
Cleton-Jansen, A-M, et al., (1991) Mol. Gen. Genet. 229, 206-212.
Murphy, L. et al. (1999) Acc. No. T36261.
Kaneko, T. et al. (1997) Acc. No. P72725.
Granger, B.L. et al. (1997) Acc. No. O00812.
NiceZyme View of Enzyme: EC 1.1.5.2, from ExPASy internet site.
Anthony, C. et al., "The pyrroloquinoline quinone (PQQ)-containing quinoprotein dehydrogenases," The Diversity of Bacterial Redox Proteins, 1998, vol. 26 (5 pgs).
Anthony, Christopher et al., "Quinoprotein-catalysed reactions," *Biochem. J.* (1996) 320, 697-711.
Anthony, Christopher et al., "The structure and function of PQQ-containing quinoproteins," Current Science, vol. 72, No. 1, May 25, 1997, pp. 716-727.
Anthony Christopher et al., "The structure and function of PQQ-containing quinoprotein dehydrogenases," Progress in Biophysics & Molecular Biology 69 (1998) 1-21.
Cleton-Janson, Anne-Marie et al., "Cloning, characterization and DNA sequencing of the gene encoding the Mr 50,000 quinoprotein glucose dehydrogenase from *Acinetobacter calcoaceticus*," Mol. Gen. Genet (1989) 217:430-436.
Cleton-Janson, Anne-Marie et al., "Cloning of the Genes Encoding the two Different Glucose Dehydrogenases from *Acinetobacter calcoaceticus*," Antonie van Leeuwenhock 56:73-79 (1989).
Cleton-Janson, Anne-Marie et al., "Cloning of the Gene Encoding Quinoprotein Glucose Dehydrogenase from *Acinetobacter calcoaceticus*: Evidence for the Presence of a Second Enzyme," Journal of Bacteriology, May 1988, p. 2121-2125.
D'Costa, E.J. et al., "Quinoprotein Glucose Dehydrogenase and its Application in an Amperometric Glucose Sensor," Biosensors 2(1986) 71-87.

(Continued)

*Primary Examiner*—Tekchand Saidha
(74) *Attorney, Agent, or Firm*—Barnes & Thornburg LLP

(57) ABSTRACT

The present invention relates to improved variants of soluble pyrroloquinoline quinone (PQQ)-dependent glucose dehydrogenases (s-GDH), to genes encoding mutated s-GDH, to mutant proteins of s-GDH with improved substrate specificity for glucose, and to different applications of these s-GDH variants, particularly for determining concentrations of sugar, especially of glucose in a sample.

11 Claims, 7 Drawing Sheets

OTHER PUBLICATIONS

Dokter, Paul et al., "Cytochome b-562 from *Acinetobacter calcoacetius* L.M.D. 79.41," Biochem. J. (1988) 254, 131-138.

Dokter, P. et al., "The in vivo and in vitro substrate specificity of quinoprotein glucose dehydrogenase of *Acinetobacter calcoaceticus* L.M.D. 79.41," FEMS Microbiology Letters 43 (1987) 195-200.

Dokter, P. et al., "Purification and characterization of quinoprotein glucose dehydrogenase from *Acinetobacter calcoaceticus* L.M.D. 79.41," Biochem. J. (1986) 239, 163-167.

Duine, J.A. et al., "Different Forms of Quinoprotein Aldose-(Glucose-)Dehydrogenase in *Acinetobacter calcoaceticus*," Arch. Microbiol. (1982) 131:27-31.

Duine, J.A. et al., "Energy Generation and the Glucose Dehydrogenase Pathway in *Acinetobacter*," The biology of *Acinetobacter*, pp. 295-312,1991.

Duine, J.A. et al., "The importance of natural diversity in redox proteins for achieving cofactor-electrode-directed electron transfer," Biosensors & Bioelectronics 10 (1995) 17-23.

Duine, Johannis A. et al., "Quinoproteins: enzymes containing the quinonoid cofactor pyrroloquinoline quinone, topaquinone or tryptophan-tryptophan quinone," Eur. J. Biochem. 200, 271-284 (1991).

Goodwin, Pat M. et al., "The Biochemistry, Physiology and Genetics of PQQ and PQQ-Containing Enzymes," Advances in Microbiol. Physiology, vol. 40, pp. 1-80, (1998).

Hill, David E. et al., "Mutagenesis with Degenerate Oligonucleotides: An Efficient Method for Saturating a Defined DNA Region with Base Pair Substitutions," Mutagenesis with Degenerate Oligonucleotides, pp. 558-568, (1999).

Igarashi, Satoshi et al., "Construction and Characterization of Mutant Water-Soluble PQQ Glucose Dehydrogenases with Altered Km Values-Site-Directed Mutagenesis Studies on the Putative Active Site," Biochemical and Biophysical Research Communications 264, 820-824 (1999).

Kaufmann, Norbert et al., "Development and evaluation of a new system for determining glucose from fresh capillary blood and heparinised venous blood," Glucotrend (18 pgs.) (1997).

Laurinavicius, Valdas et al., "A Novel Application of Heterocyclic Compounds for Biosensors Based on NAD, FAD, and PQQ Dependent Oxidoreductases," Monatshefte fur Chemie 130, 1269-1281 (1999).

Laurinavicius, V. et al., "Oxygen Insensitive Glucose Biosensor Based on PQQ-Dependent Glucose Dehydrogenase," Analytical Letters, 32(2), 299-316 (1999).

Leung, David W. et al., "A Method for Random Mutagenesis of a Defined DNA Segment Using a Modified Polymerase Chain Reaction," Technique-A Journal of Methods in Cell and Molecular Biology, vol. 1, No. 1 Aug. 1989: pp. 11-15.

Matsushita, K., Adachi, O. "Bacterial Quinoproteins Glucose Dehydrogenase and Alcohol Dehydrogenase," in Principles and Applications of Quinoproteins, 1993, 47-63, Davidson, V.L., Ed., Marcel Dekker, New York.

Matsushita, Kazunobu et al., "Quinoprotein D-glucose dehydrogenases in *Acinetobacter calcoaceticus* LMD 79:41: Purification and characterization of the membrane-bound enzyme distinct from the soluble enzyme," Antonie van Leeuwenhoek 5: 63-72 (1989).

Matsushita, Kazunobu et al., "Quinoprotein D-Glucose Dehydrogenase of the *Acinetobacter calcoaceticus* Respiratory Chain: Membrane-Bound and Soluble Forms are Different Molecular Species," Biochemistry, 1989, 28, 6276-6280.

Matsushita, Kazunobu et al., "Soluble and Membrane-Bound Quinoprotein D-Glucose Dehydrogenases of the *Acinetobacter calcoaceticus*: The Binding process of PQQ to the Apoenzymes," Biosci. Biotech. Biochem., 59 (8), 1548-1555, 1995.

Oliphant, Arnold R. et al., "Cloning of Random-Sequence Oligodeoxynucleotides," Gene, 44 (1986), 177-183.

Olsthoorn, Arjen J.J. et al., "On the Mechanism and Specificity of Soluble, Quinoprotein Glucose Dehydrogenase in the Oxidation of Aldose Sugars," Biochemistry, 1998, 37, 13854-13861.

Olsthoorn, Arjen J.J. et al., "Production, Characterization, and Reconstitution of Recombinant Quinoprotein Glucose Dehydrogenase (Soluble Type; EC 1.1.99.17) Apoenzyme of *Acinetobacter calcoaceticus*," Archives of Biochemistry and Biophysics, vol. 336, No. 1, Dec. 1, pp. 42-48, 1996.

Oubrie, Arthur et al., "Active-site structure of the soluble quinoprotein glucose dehydrogenase complexed with methylhydrazine: A covalent cofactor-inhibitor complex," PNAS Oct. 12, 1991, vol. 96, No. 21, 11787-11791.

Oubrie, Arthur et al., "Structure and mechanism of soluble quinoprotein glucose dehydrogenase," The EMBO Journal, vol. 18, No. 19, pp. 5187-5194, 1999.

Oubrie, Arthur et al., "Structural requirements of pyrroloquinoline quinone dependent enzymatic reactions," Protein Science (2000), 9:1265-1273.

Oubrie, Arthur et al., "The 1.7 A Crystal Structure of the Apo Form of the Soluble Quinoprotein Glucose Dehydrogenase from *Acinetobacter calcoaceticus* Reveals a Novel Internal Conserved Sequence Repeat," Article No. jmbi, 1999, 2766, J. Mol. Biol. (1999) 289, 319-333.

Wens, Robert et al., "A Previously Undescribed Side Effect of Icodextrin: Overestimation of Glycemia by Glucose Analyzer," Peritoneal Dialysis International, vol. 18, pp. 603-609, 1998.

Ye, Ling et al., "High Current Density 'Wired' Quinoprotein Glucose Dehydrogenase Electrode," Anal. Chem. 1993, 65, 238-241.

Database WPI, Section Ch, Week 200066, Derwent Publications Ltd., London, GB, AN 2000-679762, XP00216829.

* cited by examiner

Figure 1: DNA and protein sequence of A. calcoaceticus s-GDH
(without signalpeptide)

```
  1 GATGTTCCTCTAACTCCATCTCAATTTGCTAAAGCGAAATCAGAGAACTT  50
    ||||||||||||||||||||||||||||||||||||||||||||||||||
  1 AspValProLeuThrProSerGlnPheAlaLysAlaLysSerGluAsnPh  17

51 TGACAAGAAAGTTATTCTATCTAATCTAAATAAGCCGCACGCGTTGTTAT 100
    ||||||||||||||||||||||||||||||||||||||||||||||||||
 18 eAspLysLysValIleLeuSerAsnLeuAsnLysProHisAlaLeuLeuT  34

101 GGGGACCAGATAATCAAATTTGGTTAACTGAGCGAGCAACAGGTAAGATT 150
    ||||||||||||||||||||||||||||||||||||||||||||||||||
 35 rpGlyProAspAsnGlnIleTrpLeuThrGluArgAlaThrGlyLysIle  50

151 CTAAGAGTTAATCCAGAGTCGGGTAGTGTAAAAACAGTTTTTCAGGTACC 200
    ||||||||||||||||||||||||||||||||||||||||||||||||||
 51 LeuArgValAsnProGluSerGlySerValLysThrValPheGlnValPr  67

201 AGAGATTGTCAATGATGCTGATGGGCAGAATGGTTTATTAGGTTTTGCCT 250
    ||||||||||||||||||||||||||||||||||||||||||||||||||
 68 oGluIleValAsnAspAlaAspGlyGlnAsnGlyLeuLeuGlyPheAlaP  84

251 TCCATCCTGATTTTAAAAATAATCCTTATATCTATATTTCAGGTACATTT 300
    ||||||||||||||||||||||||||||||||||||||||||||||||||
 85 heHisProAspPheLysAsnAsnProTyrIleTyrIleSerGlyThrPhe 100

301 AAAAATCCGAAATCTACAGATAAAGAATTACCGAACCAAACGATTATTCG 350
    ||||||||||||||||||||||||||||||||||||||||||||||||||
101 LysAsnProLysSerThrAspLysGluLeuProAsnGlnThrIleIleAr 117

351 TCGTTATACCTATAATAAATCAACAGATACGCTCGAGAAGCCAGTCGATT 400
    ||||||||||||||||||||||||||||||||||||||||||||||||||
118 gArgTyrThrTyrAsnLysSerThrAspThrLeuGluLysProValAspL 134

401 TATTAGCAGGATTACCTTCATCAAAAGACCATCAGTCAGGTCGTCTTGTC 450
    ||||||||||||||||||||||||||||||||||||||||||||||||||
135 euLeuAlaGlyLeuProSerSerLysAspHisGlnSerGlyArgLeuVal 150

451 ATTGGGCCAGATCAAAAGATTTATTATACGATTGGTGACCAAGGGCGTAA 500
    ||||||||||||||||||||||||||||||||||||||||||||||||||
151 IleGlyProAspGlnLysIleTyrTyrThrIleGlyAspGlnGlyArgAs 167

501 CCAGCTTGCTTATTTGTTCTTGCCAAATCAAGCACAACATACGCCAACTC 550
    ||||||||||||||||||||||||||||||||||||||||||||||||||
168 nGlnLeuAlaTyrLeuPheLeuProAsnGlnAlaGlnHisThrProThrG 184

551 AACAAGAACTGAATGGTAAAGACTATCACACCTATATGGGTAAAGTACTA 600
    ||||||||||||||||||||||||||||||||||||||||||||||||||
185 lnGlnGluLeuAsnGlyLysAspTyrHisThrTyrMetGlyLysValLeu 200

601 CGCTTAAATCTTGATGGAAGTATTCCAAAGGATAATCCAAGTTTTAACGG 650
    ||||||||||||||||||||||||||||||||||||||||||||||||||
201 ArgLeuAsnLeuAspGlySerIleProLysAspAsnProSerPheAsnGl 217

651 GGTGGTTAGCCATATTTATACACTTGGACATCGTAATCCGCAGGGCTTAG 700
    ||||||||||||||||||||||||||||||||||||||||||||||||||
218 yValValSerHisIleTyrThrLeuGlyHisArgAsnProGlnGlyLeuA 234

701 CATTCACTCCAAATGGTAAATTATTGCAGTCTGAACAAGGCCCAAACTCT 750
    ||||||||||||||||||||||||||||||||||||||||||||||||||
235 laPheThrProAsnGlyLysLeuLeuGlnSerGluGlnGlyProAsnSer 250
```

Figure 1: Continued (second and last page)

```
 751 GACGATGAAATTAACCTCATTGTCAAAGGTGGCAATTATGGTTGGCCGAA  800
     ||||||||||||||||||||||||||||||||||||||||||||||||||
 251 AspAspGluIleAsnLeuIleValLysGlyGlyAsnTyrGlyTrpProAs  267

801 TGTAGCAGGTTATAAAGATGATAGTGGCTATGCTTATGCAAATTATTCAG  850
     ||||||||||||||||||||||||||||||||||||||||||||||||||
 268 nValAlaGlyTyrLysAspAspSerGlyTyrAlaTyrAlaAsnTyrSerA  284

851 CAGCAGCCAATAAGTCAATTAAGGATTTAGCTCAAAATGGAGTAAAAGTA  900
     ||||||||||||||||||||||||||||||||||||||||||||||||||
 285 laAlaAlaAsnLysSerIleLysAspLeuAlaGlnAsnGlyValLysVal  300

901 GCCGCAGGGGTCCCTGTGACGAAAGAATCTGAATGGACTGGTAAAAACTT  950
     ||||||||||||||||||||||||||||||||||||||||||||||||||
 301 AlaAlaGlyValProValThrLysGluSerGluTrpThrGlyLysAsnPh  317

951 TGTCCCACCATTAAAAACTTTATATACCGTTCAAGATACCTACAACTATA 1000
     ||||||||||||||||||||||||||||||||||||||||||||||||||
 318 eValProProLeuLysThrLeuTyrThrValGlnAspThrTyrAsnTyrA  334

1001 ACGATCCAACTTGTGGAGAGATGACCTACATTTGCTGGCCAACAGTTGCA 1050
     ||||||||||||||||||||||||||||||||||||||||||||||||||
 335 snAspProThrCysGlyGluMetThrTyrIleCysTrpProThrValAla  350

1051 CCGTCATCTGCCTATGTCTATAAGGGCGGTAAAAAAGCAATTACTGGTTG 1100
     ||||||||||||||||||||||||||||||||||||||||||||||||||
 351 ProSerSerAlaTyrValTyrLysGlyGlyLysLysAlaIleThrGlyTr  367

1101 GGAAAATACATTATTGGTTCCATCTTTAAAACGTGGTGTCATTTTCCGTA 1150
     ||||||||||||||||||||||||||||||||||||||||||||||||||
 368 pGluAsnThrLeuLeuValProSerLeuLysArgGlyValIlePheArgI  384

1151 TTAAGTTAGATCCAACTTATAGCACTACTTATGATGACGCTGTACCGATG 1200
     ||||||||||||||||||||||||||||||||||||||||||||||||||
 385 leLysLeuAspProThrTyrSerThrThrTyrAspAspAlaValProMet  400

1201 TTTAAGAGCAACAACCGTTATCGTGATGTGATTGCAAGTCCAGATGGGAA 1250
     ||||||||||||||||||||||||||||||||||||||||||||||||||
 401 PheLysSerAsnAsnArgTyrArgAspValIleAlaSerProAspGlyAs  417

1251 TGTCTTATATGTATTAACTGATACTGCCGGAAATGTCCAAAAAGATGATG 1300
     ||||||||||||||||||||||||||||||||||||||||||||||||||
 418 nValLeuTyrValLeuThrAspThrAlaGlyAsnValGlnLysAspAspG  434

1301 GCTCAGTAACAAATACATTAGAAAACCCAGGATCTCTCATTAAGTTCACC 1350
     ||||||||||||||||||||||||||||||||||||||||||||||||||
 435 lySerValThrAsnThrLeuGluAsnProGlySerLeuIleLysPheThr  450

1351 TATAAGGCTAAG 1362
     ||||||||||||
 451 TyrLysAlaLys  454
```

Figure 2: Amino acid sequences of A. calcoaceticus (top) and
A. baumannii (bottom)

```
  1 DVPLTPSQFAKAKSENFDKKVILSNLNKPHALLWGPDNQIWLTERATGKI  50
    |:||||.||||||.|||||||||||||||||||||||||||||||||||
  1 DIPLTPAQFAKAKTENFDKKVILSNLNKPHALLWGPDNQIWLTERATGKI  50

51 LRVNPESGSVKTVFQVPEIVNDADGQNGLLGFAFHPDFKNNPYIYISGTF 100
    ||||| ||| ||||||||||||.|||||||||||||||||.||||||||
 51 LRVNPVSGSAKTVFQVPEIVSDADGQNGLLGFAFHPDFKHNPYIYISGTF 100

101 KNPKSTDKELPNQTIIRRYTYNKSTDTLEKPVDLLAGLPSSKDHQSGRLV 150
    |||||||||||||||||||||||||.||| |||:||:||||||||||||
101 KNPKSTDKELPNQTIIRRYTYNKTTDTFEKPIDLIAGLPSSKDHQSGRLV 150

151 IGPDQKIYYTIGDQGRNQLAYLFLPNQAQHTPTQQELNGKDYHTYMGKVL 200
    ||||||||||||||||||||||||| |||||||||||||| ||||||||
151 IGPDQKIYYTIGDQGRNQLAYLFLSNQAQHTPTQQELNSKDYHTYMGKVL 200

201 RLNLDGSIPKDNPSFNGVVSHIYTLGHRNPQGLAFTPNGKLLQSEQGPNS 250
    ||||||||||||||||||||||||||||||||||  |||||||||||||
201 RLNLDGSIPKDNPSFNGVVSHIYTLGHRNPQGLAFAPNGKLLQSEQGPNS 250

251 DDEINLIVKGGNYGWPNVAGYKDDSGYAYANYSAAANKS.IKDLAQNGVK 299
    ||||||:.|||||||||||||||||||||||||||  ||| ||||||||:|
251 DDEINLVLKGGNYGWPNVAGYKDDSGYAYANYSAATNKSQIKDLAQNGIK 300

300 VAAGVPVTKESEWTGKNFVPPLKTLYTVQDTYNYNDPTCGEMTYICWPTV 349
    || |||||||||||||||||||||||||||||||||||||||| |||||||
301 VATGVPVTKESEWTGKNFVPPLKTLYTVQDTYNYNDPTCGEMAYICWPTV 350

350 APSSAYVYKGGKKAITGWENTLLVPSLKRGVIFRIKLDPTYSTTYDDAVP 399
    |||||||| |||||| ||||||||||||||||||||||||||||| |||:|
351 APSSAYVYTGGKKAIPGWENTLLVPSLKRGVIFRIKLDPTYSTTLDDAIP 400

400 MFKSNNRYRDVIASPDGNVLYVLTDTAGNVQKDDGSVTNTLENPGSLIKF 449
    ||||||||||||||:|| |||||||||||||||||||.|||||||||||
401 MFKSNNRYRDVIASPEGNTLYVLTDTAGNVQKDDGSVTHTLENPGSLIKF 450

450 TYKAK 454
    || |
451 TYNGK 455
```

Figure 3: Schematic diagram of the plasmide with gene for s-GDH (pACSGDH)
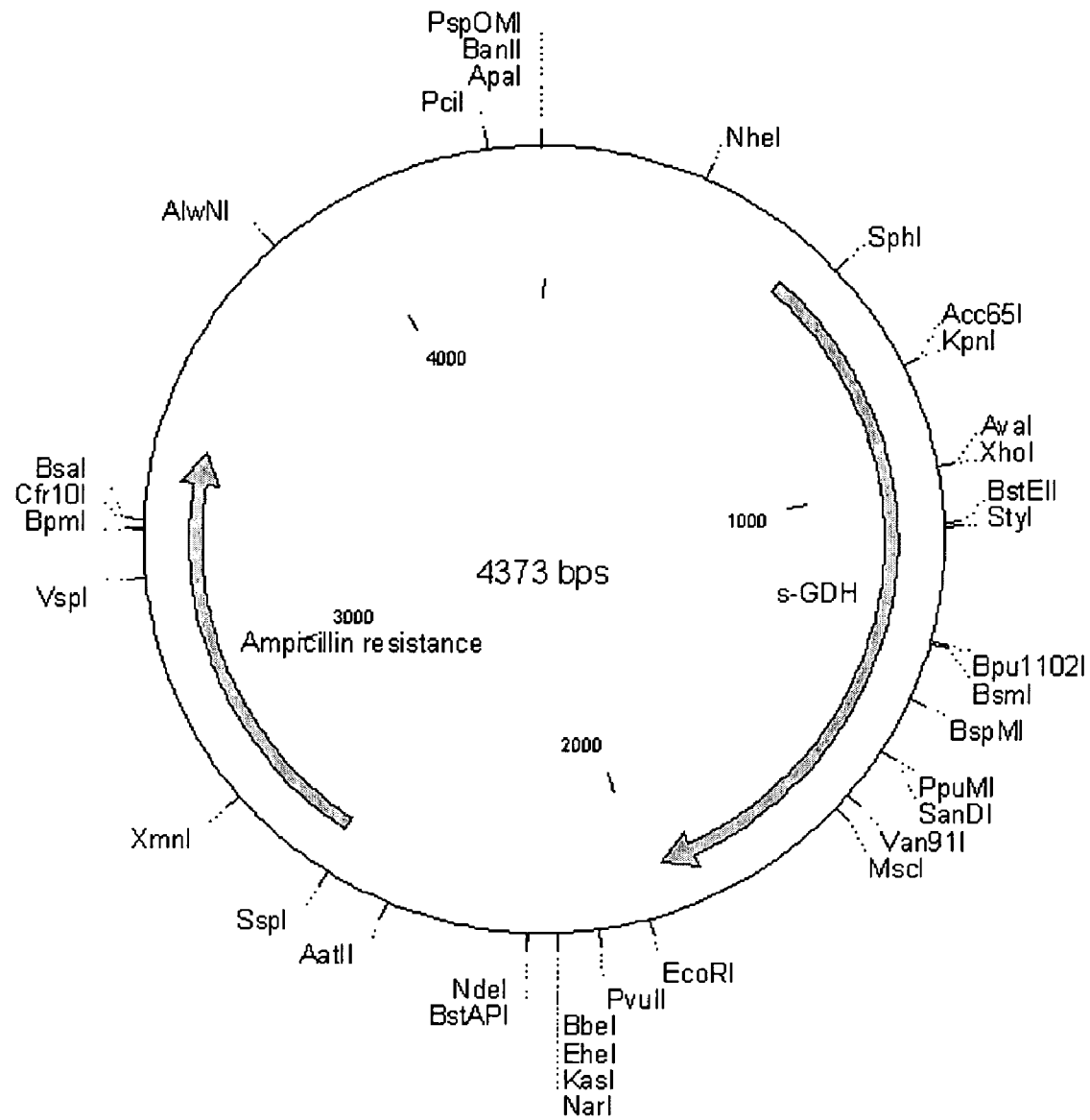

Figure 4: Nucleotide (DNA) sequence of the pACSGDH vector

```
   1  CACTAACTGA TTACGCACCG CATGTAACCG TTTTCAATCT GTGAGTAAAT
  51  TCACAGTTTA TTAACATTGT GATAGCTATG ATGACAACGT TGTCGCACT
 101  GTAACTAACG TGTAACAGTT AGTTGTCAGT TTTGCTGGGG TATTTCGCTT
 151  ATAAAAACCG TTATCACAAT ATCCCGCGAC TACCGGACAA AAATAAAGAG
 201  TTGAATAAGA GCTTATCCCA TTAGGGCTAT TTTACTTGCC ATTTTGGACC
 251  TGGGCAGTGC TCGCCAAAAC GCGTTAGCGT TTGAACGCG CTAGCGGCGG
 301  CCCGAAGGGC GAGCGTAGCG AGTCAAACCT CACGTACTAC GTGTACGCTC
 351  CGGTTTTTGC GCGCTGTCCG TGTCCAAACT GCTGCGCCAA TAACGCCTGG
 401  TGGGATAGGC TCTAAATACG CTTCGGCGTT CAGTAACACG CGTTAACGTG
 451  CTGAACAGCC GGGCATTTTT TTACGCTATA CCCTACATAA TAAAACCGGA
 501  GCTACCATGA ATAAGAAGGT ACTGACCCTT TCTGCCGTGA TGGCAAGTCT
 551  GTTATTCGGC GCGCACGCGC ATGCCGCCGA TGTTCCTCTA ACTCCATCTC
 601  AATTTGCTAA AGCGAAATCA GAGAACTTTG ACAAGAAAGT TATTCTATCT
 651  AATCTAAATA AGCCGCACGC GTTGTTATGG GGACCAGATA ATCAAATTTG
 701  GTTAACTGAG CGAGCAACAG GTAAGATTCT AAGAGTTAAT CCAGAGTCGG
 751  GTAGTGTAAA AACAGTTTTT CAGGTACCAG AGATTGTCAA TGATGCTGAT
 801  GGGCAGAATG GTTTATTAGG TTTTGCCTTC CATCCTGATT TTAAAAATAA
 851  TCCTTATATC TATATTTCAG GTACATTTAA AAATCCGAAA TCTACAGATA
 901  AAGAATTACC GAACCAAACG ATTATTCGTC GTTATACCTA TAATAAATCA
 951  ACAGATACGC TCGAGAAGCC AGTCGATTTA TTAGCAGGAT TACCTTCATC
1001  AAAAGACCAT CAGTCAGGTC GTCTTGTCAT TGGGCCAGAT CAAAAGATTT
1051  ATTATACGAT TGGTGACCAA GGGCGTAACC AGCTTGCTTA TTTGTTCTTG
1101  CCAAATCAAG CACAACATAC GCCAACTCAA CAAGAACTGA ATGGTAAAGA
1151  CTATCACACC TATATGGGTA AAGTACTACG CTTAAATCTT GATGGAAGTA
1201  TTCCAAAGGA TAATCCAAGT TTTAACGGGG TGGTTAGCCA TATTTATACA
1251  CTTGGACATC GTAATCCGCA GGGCTTAGCA TTCACTCCAA ATGGTAAATT
1301  ATTGCAGTCT GAACAAGGCC CAAACTCTGA CGATGAAATT AACCTCATTG
1351  TCAAGGTGG CAATTATGGT TGGCCGAATG TAGCAGGTTA TAAAGATGAT
1401  AGTGGCTATG CTTATGCAAA TTATTCAGCA GCAGCCAATA AGTCAATTAA
1451  GGATTTAGCT CAAAATGGAG TAAAAGTAGC CGCAGGGGTC CCTGTGACGA
1501  AAGAATCTGA ATGGACTGGT AAAAACTTTG TCCCACCATT AAAAACTTTA
```

Figure 4: Continued (second out of three pages)

```
1551  TATACCGTTC AAGATACCTA CAACTATAAC GATCCAACTT GTGGAGAGAT
1601  GACCTACATT TGCTGGCCAA CAGTTGCACC GTCATCTGCC TATGTCTATA
1651  AGGGCGGTAA AAAAGCAATT ACTGGTTGGG AAAATACATT ATTGGTTCCA
1701  TCTTTAAAAC GTGGTGTCAT TTTCCGTATT AAGTTAGATC CAACTTATAG
1751  CACTACTTAT GATGACGCTG TACCGATGTT AAGAGCAAC AACCGTTATC
1801  GTGATGTGAT TGCAAGTCCA GATGGGAATG TCTTATATGT ATTAACTGAT
1851  ACTGCCGGAA ATGTCCAAAA AGATGATGGC TCAGTAACAA ATACATTAGA
1901  AAACCCAGGA TCTCTCATTA AGTTCACCTA TAAGGCTAAG TAATACAGTC
1951  GCATTAAAAA ACCGATCTAT AAAGATCGGT TTTTTAGTT TTAGAAAAGA
2001  ATTCACTGGC CGTCGTTTTA CAACGTCGTG ACTGGGAAAA CCCTGGCGTT
2051  ACCCAACTTA ATCGCCTTGC AGCACATCCC CCTTTCGCCA GCTGGCGTAA
2101  TAGCGAAGAG GCCCGCACCG ATCGCCCTTC CCAACAGTTG CGCAGCCTGA
2151  ATGGCGAATG GCGCCTGATG CGGTATTTTC TCCTTACGCA TCTGTGCGGT
2201  ATTTCACACC GCATATGGTG CACTCTCAGT ACAATCTGCT CTGATGCCGC
2251  ATAGTTAAGC CAGCCCCGAC ACCCGCCAAC ACCCGCTGAC GCGCCCTGAC
2301  GGGCTTGTCT GCTCCCGGCA TCCGCTTACA GACAAGCTGT GACCGTCTCC
2351  GGGAGCTGCA TGTGTCAGAG GTTTTCACCG TCATCACCGA AACGCGCGAG
2401  ACGAAAGGGC CTCGTGATAC GCCTATTTTT ATAGGTTAAT GTCATGATAA
2451  TAATGGTTTC TTAGACGTCA GGTGGCACTT TTCGGGGAAA TGTGCGCGGA
2501  ACCCCTATTT GTTTATTTTT CTAAATACAT TCAAATATGT ATCCGCTCAT
2551  GAGACAATAA CCCTGATAAA TGCTTCAATA ATATTGAAAA AGGAAGAGTA
2601  TGAGTATTCA ACATTTCCGT GTCGCCCTTA TTCCCTTTTT TGCGGCATTT
2651  TGCCTTCCTG TTTTTGCTCA CCCAGAAACG CTGGTGAAAG TAAAAGATGC
2701  TGAAGATCAG TTGGGTGCAC GAGTGGGTTA CATCGAACTG GATCTCAACA
2751  GCGGTAAGAT CCTTGAGAGT TTTCGCCCCG AAGAACGTTT TCCAATGATG
2801  AGCACTTTTA AAGTTCTGCT ATGTGGCGCG GTATTATCCC GTATTGACGC
2851  CGGGCAAGAG CAACTCGGTC GCCGCATACA CTATTCTCAG AATGACTTGG
2901  TTGAGTACTC ACCAGTCACA GAAAAGCATC TTACGGATGG CATGACAGTA
2951  AGAGAATTAT GCAGTGCTGC CATAACCATG AGTGATAACA CTGCGGCCAA
3001  CTTACTTCTG ACAACGATCG GAGGACCGAA GGAGCTAACC GCTTTTTTGC
3051  ACAACATGGG GGATCATGTA ACTCGCCTTG ATCGTTGGGA ACCGGAGCTG
```

Figure 4: Continued (third and last page)

```
3101  AATGAAGCCA TACCAAACGA CGAGCGTGAC ACCACGATGC CTGTAGCAAT
3151  GGCAACAACG TTGCGCAAAC TATTAACTGG CGAACTACTT ACTCTAGCTT
3201  CCCGGCAACA ATTAATAGAC TGGATGGAGG CGGATAAAGT TGCAGGACCA
3251  CTTCTGCGCT CGGCCCTTCC GGCTGGCTGG TTTATTGCTG ATAAATCTGG
3301  AGCCGGTGAG CGTGGGTCTC GCGGTATCAT TGCAGCACTG GGGCCAGATG
3351  GTAAGCCCTC CCGTATCGTA GTTATCTACA CGACGGGGAG TCAGGCAACT
3401  ATGGATGAAC GAAATAGACA GATCGCTGAG ATAGGTGCCT CACTGATTAA
3451  GCATTGGTAA CTGTCAGACC AAGTTTACTC ATATATACTT TAGATTGATT
3501  TAAAACTTCA TTTTTAATTT AAAAGGATCT AGGTGAAGAT CCTTTTTGAT
3551  AATCTCATGA CCAAAATCCC TTAACGTGAG TTTTCGTTCC ACTGAGCGTC
3601  AGACCCCGTA GAAAAGATCA AAGGATCTTC TTGAGATCCT TTTTTTCTGC
3651  GCGTAATCTG CTGCTTGCAA ACAAAAAAAC CACCGCTACC AGCGGTGGTT
3701  TGTTTGCCGG ATCAAGAGCT ACCAACTCTT TTTCCGAAGG TAACTGGCTT
3751  CAGCAGAGCG CAGATACCAA ATACTGTCCT TCTAGTGTAG CCGTAGTTAG
3801  GCCACCACTT CAAGAACTCT GTAGCACCGC CTACATACCT CGCTCTGCTA
3851  ATCCTGTTAC CAGTGGCTGC TGCCAGTGGC GATAAGTCGT GTCTTACCGG
3901  GTTGGACTCA AGACGATAGT TACCGGATAA GGCGCAGCGG TCGGGCTGAA
3951  CGGGGGGTTC GTGCACACAG CCCAGCTTGG AGCGAACGAC CTACACCGAA
4001  CTGAGATACC TACAGCGTGA GCTATGAGAA AGCGCCACGC TTCCCGAAGG
4051  GAGAAAGGCG GACAGGTATC CGGTAAGCGG CAGGGTCGGA ACAGGAGAGC
4101  GCACGAGGGA GCTTCCAGGG GGAAACGCCT GGTATCTTTA TAGTCCTGTC
4151  GGGTTTCGCC ACCTCTGACT TGAGCGTCGA TTTTGTGAT GCTCGTCAGG
4201  GGGGCGGAGC CTATGGAAAA ACGCCAGCAA CGCGGCCTTT TTACGGTTCC
4251  TGGCCTTTTG CTGGCCTTTT GCTCACATGT TCTTTCCTGC GTTATCCCCT
4301  GATTCTGTGG ATAACCGTAT TACCGCCTTT GAGTGAGCTG ATACCGCTCG
4351  CCGCAGCCGA ACGACGGGGC CG
```

FORMS OF SOLUBLE PYRROLOQUINOLINE QUINONE-DEPENDENT GLUCOSE DEHYDROGENASE

CROSS REFERENCE TO RELATED APPLICATIONS

This is a continuation of U.S. application Ser. No. 10/319,147, filed Dec. 13, 2002, now U.S. Pat. No. 7,132,270, which is a continuation-in-part of U.S. application Ser. No. 10/082,627, filed Oct. 29, 2001, now abandoned, which is a continuation-in-part of U.S. application Ser. No. 09/710,197, filed Nov. 9, 2000, now abandoned, the complete disclosure of which is incorporated herein by reference.

BACKGROUND OF THE INVENTION

The present invention relates to improved variants of soluble pyrroloquinoline quinone (PQQ)-dependent glucose dehydrogenases (s-GDH), to genes encoding mutated s-GDH, to mutant proteins of s-GDH with improved substrate specificity for glucose, and to different applications of these s-GDH variants, particularly for determining concentrations of sugar, especially of glucose in a sample.

The International Union of Biochemistry and Molecular Biology (IUBMB) has changed the designation of PQQ-dependent glucose dehydrogenase from EC 1.1.99.17 to EC 1.1.5.2. Accordingly, hereafter, the designation of PQQ-dependent glucose dehydrogenase is recited as EC 1.1.5.2.

Two types of PQQ-dependent glucose dehydrogenase (EC 1.1.5.2) have been characterized: One is membrane-bound (m-GDH), the other is soluble (s-GDH). Both types do not share any significant sequence homology (Cleton-Jansen, A. M., et al., Mol Gen Genet 217 (1989) 430-6; Cleton-Jansen, A. M., et al., Antonie Van Leeuwenhoek 56 (1989) 73-9; Oubrie, A., et al., Proc Natl Acad Sci USA 96 (1999) 11787-91). They are also different regarding both their kinetic as well as their immunological properties (Matsushita, K., et al., Bioscience Biotechnology & Biochemistry 59 (1995) 1548-1555).

Quinoproteins use quinone as cofactor to oxidize alcohols, amines and aldoses to their corresponding lactones, aldehydes and aldolic acids (Duine, J. A. Energy generation and the glucose dehydrogenase pathway in *Acinetobacter* in "The Biology of *Acinetobacter*" (1991) 295-312, New York, Plenum Press; Duine, J. A., Eur J Biochem 200 (1991) 271-84, Davidson, V. L.—in "Principles and applications of quinoproteins" (1993) the whole book, New York, Marcel Dekker; Anthony, C., Biochem J 320 (1996) 697-711; Anthony, C. and Ghosh, M., Current Science 72 (1997) 716-727; Anthony, C., Biochem Soc Trans 26 (1998) 413-7; Anthony, C. and Ghosh, M., Prog Biophys Mol Biol 69 (1998) 1-21). Among quinoproteins, those containing the noncovalently bound cofactor 2,7,9-tricarboxy-1H-pyrrolo [2,3-f]quinoline-4,5-dione (PQQ) constitute the largest sub-group (Duine 1991, supra). All bacterial glucose dehydrogenases known so far belong to this sub-group with PQQ as the prosthetic group (Anthony and Ghosh 1997, supra, Goodwin and Anthony 1998, supra).

In bacteria, there are two completely different types of PQQ-dependent glucose dehydrogenases (EC1.1.5.2): the soluble type (s-GDH) and the membrane-bound type (m-GDH) (Duine et al., 1982; Matsushita et al., 1989a,b). The m-GDHs are widespread in Gram-negative bacteria, s-GDHs, however, have been found only in the periplasmic space of *Acinetobacter* strains, like *A. calcoaceticus* (Duine, 1991a; Cleton-Jansen et al., 1988; Matsushita and Adachi, 1993) and *A. baumannii* (JP 11243949).

Through searching sequence databases, two sequences homologous to the full-length *A. calcoaceticus* s-GDH have been identified in *E. coli* K-12 and *Synechocystis* sp. Additionally, two incomplete sequences homologous to *A. calcoaceticus* s-GDH were also found in the genome of *P. aeruginosa* and *Bordetella pertussis* (Oubrie et al. 1999a), respectively. The deduced amino acid sequences of these four uncharacterized proteins are closely related to *A. calcoaceticus* s-GDH with many residues in the putative active site absolutely conserved. These homologous proteins are likely to have a similar structure and to catalyze similar PQQ-dependent reactions (Oubrie et al., 1999a).

Bacterial s-GDHs and m-GDHs have been found to possess quite different sequences and different substrate specificity. For example, *A. calcoaceticus* contains two different PQQ-dependent glucose dehydrogenases, one m-GDH which is active in vivo, and the other designated s-GDH for which only in vitro activity can be shown. Cleton-Jansen et al., (1988; 1989a,b) cloned the genes coding for the two GDH enzymes and determined the DNA sequences of both these GDH genes. There is no obvious homology between m-GDH and s-GDH corroborating the fact that m-GDH and s-GDH represent two completely different molecules.

The gene of s-GDH from *A. calcoaceticus* has been cloned in *E. coli* behind a leader sequence and a strong promoter. After being synthesized in the cell, the s-GDH is translocated through the cytoplasmic membrane into the periplasmic space (Duine, J. A. Energy generation and the glucose dehydrogenase pathway in *Acinetobacter* in "The Biology of *Acinetobacter*" (1991) 295-312, New York, Plenum Press, Matsushita, K. and Adachi, O. Bacterial quinoproteins glucose dehydrogenase and alcohol dehydrogenase in "Principles and applications of Quinoproteins" (1993) 47-63, New York, Marcel Dekker). Like the native s-GDH from *A. calcoaceticus*, s-GDH expressed in *E. coli* is also a homodimer, with one PQQ molecule and three calcium ions per monomer (Dokter et al., 1986 supra,1987 supra 1988 supra; Olsthoorn, A. and J. Duine, J. A., Arch Biochem Biophys 336 (1996) 42-8; Oubrie, A., et al., J Mol Biol 289 (1999) 319-33, Oubrie, A., et al., Proc Natl Acad Sci USA 96 (1999) 11787-91, Oubrie, A., et al., Embo J 18 (1999) 5187-94). s-GDH oxidizes a wide range of mono- and disaccharides to the corresponding ketones which further hydrolyze to the aldonic acids, and it is also able to donate electrons to PMS (phenazine metosulfate), DCPIP (2,6-dichlorophenolindophenol), WB (Wurster's blue) and short-chain ubiquinones such as ubiquinone Q1 and ubiquinone Q2 (Matsushita, K., et al., Biochemistry 28 (1989) 6276-80; Matsushita, K., et al., Antonie Van Leeuwenhoek 56 (1989) 63-72), several artificial electron acceptors such as N-methylphenazonium methyl sulfate (Olsthoorn, A. J. and Duine, J. A., Arch Biochem Biophys 336 (1996) 42-8; Olsthoorn, A. J. and Duine, J. A., Biochemistry 37 (1998) 13854-61) and electroconducting polymers (Ye, L., et al., Anal. Chem. 65 (1993) 238-41).

In view of s-GDH's high specific activity towards glucose (Olsthoorn, A. J. and Duine, J. A., Arch Biochem Biophys 336 (1996) 42-8) and its broad artificial electron acceptor specificity, the enzyme is well suited for analytical applications, particularly for being used in (bio-)sensor or test strips for glucose determination in diagnostic applications (Kaufmann et al., 1997 supra).

Glucose oxidation can be catalyzed by at least three quite distinct groups of enzymes, i.e., by NAD-dependent, dye-linked glucose dehydrogenases, by flavoprotein glucose oxidase or by quinoprotein GDHs (Duine 1995). A rather slow autooxidation of reduced s-GDH has been observed, demonstrating that oxygen is a very poor electron acceptor for s-GDH (Olsthoorn and Duine 1996). s-GDH can efficiently donate electrons to PMS, DCPIP, WB and short-chain ubiquinones such as Q1 and Q2, but it can not efficiently donate electrons directly to oxygen.

Traditional test strips and sensors for monitoring glucose level in blood, serum and urine e. g. from diabetic patients use glucose oxidase. However, since glucose oxidase transfers its electrons to oxygen, it is known that oxygen may have a negative impact on glucose measurements which are based on this enzyme. The major advantage of PQQ-dependent glucose dehydrogenases is their independence from oxygen. This important feature is e.g., discussed in U.S. Pat. No. 6,103,509, in which some features of membrane-bound GDH have been investigated.

An important contribution to the field has been the use of s-GDH together with appropriate substrates. Assay methods and test strip devices based on s-GDH are disclosed in detail in U.S. Pat. No. 5,484,708. This patent also contains detailed information on the set-up of assays and the production of s-GDH-based test strips for measurement of glucose. The methods described there as well in the cited documents are herewith included by reference.

Other patents or applications relating to the field and comprising specific information on various modes of applications for enzymes with glucose dehydrogenase activity are U.S. Pat. No. 5,997,817; U.S. Pat. No. 6,057,120; EP 620 283; and JP 11-243949-A.

A commercial system which utilizes s-GDH and an indicator that produces a color change when the reaction occurs (Kaufmann et al. 1997) is the Glucotrend® system distributed by Roche Diagnostics GmbH.

Despite the above discussed important advantages there also is a major inherent problem of s-GDH. s-GDH has rather a broad substrate spectrum as compared to m-GDH. That is, s-GDH oxidizes not only glucose but also several other sugars including maltose, galactose, lactose, mannose, xylose and ribose (Dokter et al. 1986a). The reactivity towards sugars other than glucose may in certain cases impair the accuracy of determining blood glucose levels, in some diabetic patients. In particular patients on peritoneal dialysis treated with icodextrin (a glucose polymer) may contain in their body fluids, e.g., in blood, high levels of other sugars, especially maltose (Wens, R., et al., Perit Dial Int 18 (1998) 603-9).

Therefore clinical samples, as e.g. obtained from diabetic patients, especially from patients with renal complications and especially from patients under dialysis may contain significant levels of other sugars, especially maltose. Glucose determinations in samples obtained from such critical patients may be impaired by maltose.

There are scarce reports in the literature on attempts to produce modified PQQ-dependent s-GDHs which exhibit altered substrate specificity. Due to a negative outcome most of these efforts have not been published. Igarashi, S., et al., (1999) report that introducing a point mutation at position Glu277 leads to mutants with altered substrate specificity profile. However, none of these mutants, lead to an at least two-fold increased improved specificity for glucose as e.g., compared to xylose, galactose or maltose.

It can be summarized that the attempts known in the art aiming at improvements of properties of s-GDH, especially its specificity towards glucose, have not been successful to the extend required for accurate monitoring of glucose levels in patients having also high levels of sugars other than glucose.

A great demand and clinical need therefore exists for mutant forms of s-GDH which feature an improved specificity for glucose as substrate.

It was the task of the present invention to provide new mutants or variants of s-GDH with significantly improved substrate specificity for glucose as compared to other selected sugar molecules, e.g., like galactose or maltose.

Surprisingly it has been found that it is possible to significantly improve the substrate specificity of s-GDH for glucose, as compared to other sugars, and to at least partially overcome the above described problems known in the art.

The substrate specificity for glucose as compared to other selected sugar molecules has been significantly improved by providing mutant s-GHD according to the present invention as described herein below and in the appending claims. Due to the improved substrate specificity of the new forms of s-GDH, significant technical progress for glucose determinations in various fields of applications is possible.

SUMMARY OF THE INVENTION

It has now surprisingly been found that it is possible to provide s-GDH mutants with improved substrate specificity towards glucose as a substrate as compared to other selected sugars. New s-GDH variants are disclosed which exhibit a significant higher substrate specificity for glucose, especially as compared to maltose.

Also disclosed are mutant s-GDH molecules, which, compared to the wild-type enzyme, exhibit essentially equal specific activity for glucose as substrate but markedly reduced activity for other selected sugar molecules.

Such comparison of a mutant's specific activity for one of the various other substrate molecules is based on and calculated in relation to the original enzymatic activities of a wild-type enzyme, e.g., as isolated from *Acinetobacter calcoaceticus*.

Mutated s-GDH proteins as well as polynucleotide-sequences coding for such proteins exhibiting improved properties, especially increased specificity for glucose are also provided.

s-GDH mutants comprising at least one amino acid substitutions at an amino acid position corresponding to a position of the s-GDH wild-type sequence known from *A. calcoaceticus* (SEQ ID NO: 24) selected from the group consisting of positions 348 and 428 have been found to provide for s-GDH enzymes with improved properties, especially with improved specificity for glucose. Variants comprising a substitution at position 348 exhibit a strikingly positive effect on glucose specificity.

The improved s-GDH mutants can be used with great advantage for the specific detection or measurement of glucose in biological samples, especially in tests strip devices or in biosensors.

The following examples, references, sequence listing and figures are provided to aid the understanding of the present invention, the true scope of which is set forth in the appended claims. It is understood that modifications can be made in the procedures set forth without departing from the spirit of the invention.

DESCRIPTION OF THE FIGURES

FIG. 1: Nucleotide (DNA) sequence of the *Acinetobacter calcoaceticus* PQQ-dependent soluble glucose dehydrogenase gene (SEQ ID NO: 23) and the corresponding amino acid sequence (SEQ ID NO: 24).

FIG. 2: Protein sequences of *A. calcoaceticus* PQQ-dependent s-GDH (top, SEQ ID NO: 24) and *A. baumannii* s-GDH (bottom) aligned according to sequence homology.

FIG. 3: Illustration of pACSGDH vector referred to in Example 1 containing the wild-type or mutated DNA sequences of soluble PQQ-dependent glucose dehydrogenase.

FIG. 4: Nucleotide (DNA) sequence of the pACSGDH vector referred to in Example 1 (SEQ ID NO: 25) containing the wild-type DNA sequence of soluble PQQ-dependent glucose dehydrogenase (SEQ ID NO: 23).

DETAILED DESCRIPTION OF THE INVENTION

In a first embodiment the invention relates to a mutant of the soluble form of EC 1.1.5.2 also known as PQQ-dependent soluble glucose dehydrogenase (s-GDH), said mutant characterized in that relative to the corresponding wild-type enzyme and with regard to at least one other selected sugar substrate, it has an at least two-fold improved substrate specificity for glucose.

The directions given in this invention are easily applied for any known or even yet un-known isolate of s-GDH. These wild-type isolates can be used to assess the relative improvements in specificity for the variants generated therefrom.

The wild-type enzyme of *Acinetobacter calcoaceticus*-type strain LMD 79.41 which corresponds to SEQ ID NO: 24 is well-known and well-characterized. In case a different wild-type enzyme under investigation is not well-characterized it is advantageous to use the s-GDH from *Acinetobacter calcoaceticus*-type strain LMD 79.41 as a reference. In a further preferred embodiment the properties of an improved variant of s-GDH are compared to this wild-type enzyme. The present invention therefore also relates to a mutant of s-GDH said mutant characterized in that relative to the wild-type enzyme of SEQ ID NO: 24 and with regard to at least one other selected sugar substrate, it has an at least two-fold increased substrate specificity for glucose.

As discussed above, two completely different enzyme families with glucose dehydrogenase activity, grouped together under EC 1.1.5.2, are characterized to date. These two enzyme families, however, appear not to be related to each other.

For the purpose of this invention only the soluble form of GDH (s-GDH) is relevant and improved variants thereof are discussed herein below.

It is known in the art that the wild-type DNA-sequence of a soluble PQQ-dependent glucose dehydrogenase can be isolated from strains of *Acinetobacter*. Most preferred is the isolation from *Acinetobacter calcoaceticus*-type strain LMD 79.41. The sequence of this wild-type s-GDH (the mature protein) is given in FIG: 1 and SEQ ID NO: 24. Other LMD strains of *Acinetobacter* may also be used as source of wild-type s-GDH. Such sequences can be aligned to the sequence obtained from *A. calcoaceticus* and sequence comparisons be made (see FIG: 2). It also appears feasible to screen DNA-libraries of other bacterial strains, as for example described for *E. coli* K-12 (Oubrie, A., et al., J Mol Biol 289 (1999) 319-33) above and to identify sequences related to s-GDH in such genomes. Such sequences and yet unidentified homologous sequences may be used to generate s-GDH mutants with improved substrate specificity for glucose.

The term "mutant" or "variant" in the sense of the present invention relates to a s-GDH protein which compared to a corresponding wild-type sequence exhibits at least one amino acid substitution. The expert in the field will appreciate that there are various possibilities to produce polynucleotides encoding for a polypeptide sequence of such mutated s-GDH. It is of course also possible to generate mutants comprising one or more additions or deletions of amino acids.

A mutant according to the present invention is characterized in that relative to the corresponding wild-type enzyme it has at least a two-fold improved substrate specificity for glucose as compared to at least one other selected sugar substrate.

In order to calculate the substrate specificity or cross-reactivity one easy way is to set the activity measured with glucose as substrate to 100% and to compare the activity measured with the other selected sugar to the glucose value. Sometimes, in order not to be redundant, simply the term specificity is used without making special reference to glucose on the one hand and a selected other sugar substrate on the other hand.

The expert in the field will appreciate that comparison of (re-)activities is best made at equimolar concentrations of the substrate molecules investigated using well-defined assay conditions. Otherwise corrections for differences in concentrations have to be made.

Standardized and well-defined assay conditions have to be chosen in order to assess (improvements in) specificity. The enzymatic activity of s-GDH for glucose as substrate as well as for other selected sugar substrates is measured as described in Example 6.

Based on these measurements cross-reactivity and (improvements in) specificity are assessed.

The s-GDH (cross-)reactivity for a selected sugar in percent is calculated as

Cross-reactivity [%]=(activity selected sugar/activity glucose)×100%.

(Cross-)reactivity for maltose of wild-type s-GDH according to the above formula has been determined as about 105%. Wild-type s-GDH (cross-)reactivity for galactose has been measured as about 50% (cf. Table 1).

(Improved) specificity is calculated according to the following formula:

$$\text{specificity(improvement)} = \frac{\text{activity glucose mutant}}{\text{activity glucose wild-type}} \times \frac{\text{activity selected sugar wild-type}}{\text{activity selected sugar mutant}}$$

As compared to the wild-type enzyme, a s-GDH form with an at least two-fold improvement in specificity for glucose versus maltose (maltose/glucose) accordingly with maltose as substrate has at most 52,5% of the activity as measured with glucose as substrate. Or, if, for example, a mutant s-GDH has a cross-reactivity for maltose of 20% (determined and calculated as described above), this mutant as compared to the wild-type s-GDH therefore has a 5.25 fold improved substrate specificity (maltose/glucose).

The term "specific activity" for a substrate is well known in the art, it is preferably used to describe the enzymatic activity per amount of protein. Various methods are known to the art to determine specific activity of GDH molecules, using glucose or other sugars as substrates (Igarashi, S., et al., Biochem Biophys Res Commun 264 (1999) 820). One of the methods available for such measurement is described in detail in the examples section.

Whereas it is possible, to select many different sugar molecules and to investigate the glucose specificity of s-GDH in comparison to any such selected sugar molecule, it is preferred to select a clinically relevant sugar molecule for such a comparison. Preferred selected sugars are selected from the group consisting of mannose, allose, galactose, xylose, and maltose. More preferably, maltose or galactose are selected and mutant s-GDH is tested for improved substrate specificity for glucose as compared to galactose or maltose. In a further preferred embodiment the selected sugar is maltose.

It has surprisingly been found that the improvements in glucose specificity of mutated s-GDH, e.g., for maltose vs. glucose, are quite considerable. It is therefore further preferred that said substrate specificity for glucose as compared to the substrate specificity for at least one of the selected other sugar substrates is improved at least three-fold. Other preferred embodiments comprise s-GDH mutants characterized by an improved substrate specificity for glucose, which is at least 5 times higher or also preferred at least 10 times higher, as compared to the other sugar molecule selected.

Mutations in s-GDH lead in many cases to enzyme variants with drastically reduced specific activity for the substrate glucose. Such decrease in (absolute or overall) specific activity for the substrate glucose, however, may be critical for routine applications. Surprisingly it has been found that improved specificity for glucose must not go to the expense of a dramatically reduced overall specific activity. It is therefore preferred that the s-GDH with improved specificity towards the substrate glucose exhibits at least 10% of the specific activity for glucose as measured with the wild-type enzyme. It is of course more preferred that such mutated enzymes exhibit at least 20% or more preferred at least 50% of the respective glucose activity of wild-type s-GDH.

In a further preferred embodiment, the invention relates to a mutant of the soluble form of EC 1.1.5.2 also known as PQQ-dependent soluble glucose dehydrogenase (s-GDH), said mutant characterized in that the substrate specific reactivity towards glucose is essentially equal to that of the wild-type enzyme and the substrate specific reactivity towards maltose is 30% or less as compared to the wild-type enzyme.

The substrate specific reactivity (also termed specific activity) towards glucose is considered to be essentially equal to that of the wild-type enzyme if at least 50% of the original enzymatic activity for glucose of the wild-type enzyme is maintained. Also preferred are mutants exhibiting at least 80% or more preferred, at least 90% of the specific activity for glucose as measured for the wild-type enzyme.

Quite surprisingly it has been found, that it is possible to obtain such s-GDH mutants or variants, which compared to the wild-type s-GDH exhibit essentially equal enzymatic activity for glucose but, nonetheless, significantly reduced substrate specific reactivity towards other selected sugars, especially towards maltose. Mutants characterized in that the substrate specific reactivity towards glucose is essentially equal to that of the wild-type enzyme and in that the substrate specific reactivity towards maltose is 20% or less as compared to the wild-type enzyme are preferred. Further preferred are such mutants for which the maltose specific activity is 15% or even only 10% or less of the maltose specific activity as measured for the corresponding wild-type enzyme, whereas the specific reactivity for glucose is essentially equal to the specific activity for glucose of the corresponding wild-type enzyme.

In case the wild-type enzyme is not well-characterized it is preferred to use the s-GDH from *Acinetobacter calcoaceticus*-type strain LMD 79.41 as reference. In a further preferred embodiment the properties of an improved variant of s-GDH are compared to this wild-type enzyme and the present invention therefore relates to a mutant of s-GDH said mutant characterized in that relative to the wild-type enzyme of SEQ ID NO: 24 it exhibits essentially equal enzymatic activity for glucose but, significantly reduced (at least 70% less) substrate specific reactivity towards at least one other selected sugar substrate.

Unexpectedly it has been found that it is possible to generate s-GDH mutants with improved substitute specificity and even more unexpectedly it has been found that it is only a few well-defined amino acid positions which are of major relevance in that respect.

The achievements of the present invention are described in great detail by making reference to amino acid positions known from SEQ ID NO: 24, the wild-type sequence of s-GDH as isolated from *Acinetobacter calcoaceticus*-type strain LMD 79.41. Amino acid positions in different s-GDH isolates corresponding to positions of SEQ ID NO: 24 are easily identified by appropriate sequence comparison. Preferably the PileUp program is used to assess homology or identity between such sequences. The amino acid positions given herein below shall be understood as amino acid positions of SEQ ID NO: 24 or of positions corresponding thereto in other s-GDH molecules, unless specific reference is made to a different SEQ ID NO or to a different s-GDH isolate. In order to avoid redundances only in a few cases a specific hind to the fact that corresponding positions in different isolates can be modified in the same way is given, whereas for convenience in most cases simply and only the corresponding position from SEQ ID NO: 24 is used.

Mutants comprising an amino acid substitution at the position corresponding to position 348 of s-GDH have been found to exhibit a striking effect on specificity for glucose. As demonstrated in table 1, a variety of s-GDH variants with improved specificity for glucose can be identified and generated, as long as at least the amino acid in position threonine 348—as corresponding to wild-type s-GDH sequence position from *A. calcoaceticus*—is substituted with an appropriate other amino acid.

A preferred embodiment of the present invention therefore relates to a mutant protein of PQQ-dependent s-GDH comprising an amino acid residue substitution at the amino acid position corresponding to position 348 of the s-GDH wild-type sequence known from *A. calcoaceticus* (SEQ ID NO: 24).

It has also been found, that combined substitutions of amino acids at amino acid positions corresponding to positions 348 and 428 of SEQ ID NO: 24 are advantageous to generate s-GDH mutants or variants with significantly improved specificity for glucose.

Residues 348 or 428 of s-GDH as isolated from *Acinetobacter calcoaceticus*-type strain LMD 79.41 are not known from the art to contribute to the substrate binding of s-GDH (Oubrie, A., et al., Embo J 18 (1999) 5187-94,; Oubrie, A. and Dijkstra, B. W., Protein Sci 9 (2000) 1265-73). No chemical or physical explanation is at hand, why substitutions of these amino acid residues alters the substrate specificity of s-GDH for glucose as compared to other sugar molecules of interest.

It has been found in addition that substitution of amino acid 76 also has a positive effect on glucose specificity of s-GDH.

In a further preferred embodiment the mutated s-GDH is characterized in that the amino acid residue threonine at position 348 is substituted with an amino acid residue selected from the group consisting of alanine, glycine, and serine. In a most preferred embodiment glycine is used to substitute for threonine at position 348.

One group of preferred s-GDH variants according to this invention comprises a substitution of the amino acid residue at position 348 and at at least one of the following positions 76, 143, 168, 169 and 428.

In yet a further embodiment a mutant protein of PQQ-dependent s-GDH comprises an amino acid residue substitution at position 428 of the correspondent wild-type sequence from *Acinetobacter calcoaceticus*, in which the asparagine residue of the wild-type sequence is replaced by other appropriate amino acid residues. Preferably, such amino acid residue is selected from the group consisting of leucine, proline and valine. It is preferred to substitute the asparagine at position 428 with proline.

It further has proved that the amino acid glutamine at position 76 can be substituted to improve on the problems imposed by s-GDH cross-reactivity with other sugar molecules. Sequence positions of other s-GDH isolates corresponding to this sequence position are easily identified by a homology search based on SEQ ID NO:3. In another preferred embodiment the mutant according to the present invention therefore comprises a substitution of glutamine at position 76 of the corresponding wild-type sequence from *Acinetobacter calcoaceticus*.

It is preferred to select the amino acid used in such substitution at a position corresponding to position 76 in SEQ ID NO: 24 from the group consisting of alanine, aspartic acid, glutamic acid, glycine, methionine, proline and serine.

As described above, a substitution of the amino acid in position 348 of the s-GDH sequence corresponding to the wild-type sequence isolated from *A. calcoaceticus*, can be used to significantly improve the glucose specificity of s-GDH. Further improved mutants are obtained by providing a mutant s-GDH protein comprising at least two amino acid substitutions, wherein the amino acid corresponding to amino acid position 348 of SEQ ID NO: 24 is substituted.

A further embodiment of the present invention therefore is a mutant s-GDH comprising at least two amino acid residue substitutions at an amino acid position corresponding to a position of the s-GDH wild-type sequence known from *A. calcoaceticus* (SEQ ID NO: 24), said substituted amino acid positions being selected from the group consisting of positions 16, 22, 76, 116, 120, 127, 143, 168, 169, 171, 177, 227, 230, 231, 245, 255, 277, 295, 299, 308, 317, 341, 348, 349, 355, 422, 428 and 438, wherein the amino acid residue T348 is replaced. It is further preferred, that a s-GDH variant with the at least two substituted amino acid residues comprises a substitution in position 348 and at least one additional substitution selected from the group of positions comprising positions 76, 143, 168, 169, and 428.

In a further preferred embodiment the at least two amino acid positions which are substituted in a mutant s-GDH are selected from the group consisting of amino acid positions 76, 348, and/or 428.

Mutants comprising substitutions at amino acid residues corresponding to positions 348 and 428 have been found as very advantageous for improving the specificity of s-GDH for glucose in comparison to other sugar substrates. It is especially preferred to design and select mutants of s-GDH, which comprise a substitution at both the positions 348 and 428. Most preferred are mutants comprising the preferred substitutions as described above at both these positions. A s-GDH variant comprising T348G and N428P is most preferred.

The terminology T348G and N428P is known to the art to indicate that threonine at position 348 is replaced by glycine and asparagine at position 428 is replaced by proline.

Mutant s-GDH proteins comprising in addition to substitutions at positions 348 and 428 also substitutions at positions 76, 127 and 143, also represent preferred embodiments of the present invention.

Further preferred examples of mutated s-GDH proteins according to the present invention comprise amino acid substitutions at positions 76 and 348 and also such mutants comprising substitutions at positions 76 and 428. In yet another preferred embodiment the mutated s-GDH protein according to the present invention comprises substitutions of the amino acid residues at positions 76, 348 and 428.

In yet a further preferred embodiment the s-GDH variant according to the present invention comprises at least three amino acid substitutions, the at least three substituted amino acid residues corresponding to amino acid positions of the s-GDH wild-type sequence known from *A. calcoaceticus* (SEQ ID NO: 24), said substituted amino acid positions being selected from the group consisting of positions 171, 227, 230, 245, 341, 348, 349, and 428, wherein both the amino acid residues T348 and N428 are substituted. Preferably such trible mutants comprise at least one of the following substitutions: Y171G, H227F, P230H, E245D or M341V.

Preferred s-GDH variants with highly improved specificity for glucose comprise substitutions at positions 348 and 428 in combination with substitutions at positions 245 or 341, or both.

Amino acid sequence analysis revealed that the sequence motives found in wild-type s-GDH from *A. calcoaceticus* on the one hand and *A. baumannii* on the other hand appear to be very conservative around the positions of major relevance to improve the specificity for glucose as identified in the present invention, i.e. positions 76, 348, and 428, as corresponding to wild-type s-GDH from *A. calcoaceticus* (c.f., FIG. 2).

A preferred embodiment according to the present invention therefore is a mutant protein of PQQ-dependent s-GDH comprising the amino acid sequence of WPX$aa$VAPS (SEQ ID NO: 1), wherein said X$aa$ residue is an amino acid residue other than threonine. SEQ ID NO:1 corresponds to position 346-352 of *A. calcoaceticus* wild-type s-GDH or position 347-353 of *A. baumannii* wild-type s-GDH.

Further preferred is an s-GDH mutant wherein said X$aa$ in SEQ ID NO: 1 represents alanine, glycine or serine, most preferred, X$aa$ represents glycine.

A mutant of PQQ-dependent s-GDH, comprising the amino acid sequence of TAGX$aa$VQK (SEQ ID NO: 2), wherein said X$aa$ residue is an amino acid residue other than asparagine, is another preferred embodiment of the invention. SEQ ID NO:2 corresponds to position 425-431 of *A. calcoaceticus* wild-type s-GDH or to position 426-432 of *A. baumannii* wild-type s-GDH.

Preferably the s-GDH mutant comprising SEQ ID NO:2 is characterized in that said X$aa$ residue is selected from the group consisting of leucine, proline and valine, most preferred X$aa$ is a proline residue.

Numerous possibilities are known in the art to produce mutant proteins. Based on the important findings of the present invention disclosing the critical importance of amino acid positions 348 and 428 and also the utility of position 76, the skilled artisan now can easily produce further appropriate variants of s-GDH. Such variants for example can be obtained by the methods known as random mutagenesis (Leung, D. W., et al., Technique 1 (1989) 11-15) and/or directed mutagenesis (Hill, D. E., et al., Methods Enzymol 155 (1987) 558-68). An alternative method to produce a protein with the desired properties is to provide chimaeric constructs, which contain sequence elements from at least two different sources or to completely synthesize an appropriate s-GDH gene. Such procedures known in the art may be used in combination with the information disclosed in the present invention to provide mutants or variants of s-GDH comprising at least one amino acid substitution at a sequence position corresponding to positions 348, and/or 428 of SEQ ID NO: 24.

A s-GDH variant according to the present invention can e.g., be produced by starting from a s-GDH gene as isolated from *Acinetobacter calcoaceticus*-type strain LMD 79.41 as well as by starting from a homologous sequence. In the context of this application the term "homologous" is meant to comprise wild-type s-GDH as isolated from other microorganisms, provided that the sequence homology as compared to SEQ ID NO: 24 is at least 90%. With other words, after appropriate alignment using the PileUp program, at least 90% of the amino acids of that s-GDH are identical to the amino acids described in SEQ ID NO: 24.

It will be understood that variations of DNA and amino acid sequences naturally exist, or may be intentionally introduced using methods known in the art. These variations may result in up to 10% amino acid differences in the overall sequence, due to deletions, substitutions, insertions, inversions or additions of one or more amino acid residues in said sequence as compared to SEQ ID NO: 24. Such amino acid substitutions may be made, for example, on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine, asparagine, glutamine, serine, threonine, phenylalanine, tyrosine. Other contemplated variations include salts and esters of the afore mentioned polypeptides, as well as precursors of the aforementioned polypeptides, for example, precursors having N-terminal substitution such as methionine, N-formylmethionine used as leader sequences. Such variations may be made without necessarily departing from the scope and the spirit of the present invention.

According to procedures known in the state of the art or according to the procedures given in the examples section, it is possible to obtain polynucleotide sequences coding for any of the s-GDH mutants as discussed above. The invention therefore comprises also isolated polynucleotide sequences encoding s-GDH mutant proteins as described above.

The present invention further includes an expression vector comprising a nucleic acid sequence according to the present invention operably linked to a promoter sequence capable of directing its expression in a host cell.

The present invention further includes an expression vector comprising a nucleic acid sequence according to the present invention operably linked to a promoter sequence capable of directing its expression in a host cell. Preferred vectors are plasmids such as pACSGDH shown in FIGS. 3 and 4.

Expression vectors useful in the present invention typically contain an origin of replication, a promoter located upstream in the DNA sequence and are followed by the DNA sequence coding for all or part of s-GDH variants. The DNA sequence coding for all or part of the s-GDH variants is followed by transcription termination sequences and the remaining vector. The expression vectors may also include other DNA sequences known in the art, for example, stability leader sequences which provide for stability of the expression product, secretory leader sequences which provide for secretion of the expression product, sequences which allow expression of the structural gene to be modulated (e.g., by the presence or absence of nutrients or other inducers in the growth medium), marking sequences which are capable of providing phenotypic selection in transformed host cells, and the sequences which provide sites for cleavage by restriction endonucleases.

The characteristics of the actual expression vector used must be compatible with the host cell, which is to be employed. For example, when cloning in an *E. coli* cell system, the expression vector should contain promoters isolated from the genome of *E. coli* cells (e.g., , lac, or trp). Suitable origins of replication in *E. coli* various hosts include, for example, a ColE1 plasmid replication origin. Suitable promoters include, for example, lac and trp. It is also preferred that the expression vector includes a sequence coding for a selectable marker. The selectable marker is preferably an antibiotic resistance gene. As selectable markers, ampicillin resistance, or canamycin resistance may be conveniently employed. All of these materials are known in the art and are commercially available.

Suitable expression vectors containing the desired coding and control sequences may be constructed using standard recombinant DNA techniques known in the art, many of which are described in Sambrook et al. (1989).

The present invention additionally concerns host cells containing an expression vector which comprises a DNA sequence coding for all or part of the mutant s-GDH. The host cells preferably contain an expression vector that comprises all or part of one of the DNA sequences having one or more mutations shown in Table 1. Further preferred are the host cells containing an expression vector comprising one or more regulatory DNA sequences capable of directing the replication and/or the expression of, and operatively linked to a DNA sequence coding for, all or part of mutant s-GDH. Suitable host cells include, for example, *E. coli* HB101 (ATCC 33694) available from Pomega (2800 Woods Hollow Road, Madison, Wis., USA), XL1-Blue MRF available from Stratagene (11011 North Torrey Pine Road, La Jolla, Calif., USA) and the like.

Expression vectors may be introduced into host cells by various methods known in the art. For example, transformation of host cells with expression vectors can be carried out by polyethylene glycol mediated protoplast transformation method (Sambrook et al. 1989). However, other methods for introducing expression vectors into host cells, for example, electroporation, biolistic injection, or protoplast fusion, can also be employed.

Once an expression vector containing an s-GDH variant has been introduced into an appropriate host cell, the host cell may be cultured under conditions permitting expression of the desired s-GDH variants. Host cells containing an expression vector which contains a DNA sequence coding for all or part of the mutant s-GDH are, e.g., identified by one or more of the following general approaches: DNA hybridization, the presence or absence of marker gene functions, assessment of the level of transcription as measured by the production of s-GDH mRNA transcripts in the host cell, and detection of the gene product immunologically. Preferably transformed host cells are identified by enzyme assay, e.g., colourimetric detection.

The present invention also teaches the generation and screening of s-GDH variants. Random mutagenesis and saturation mutagenesis is performed as known in the art. Variants are analyzed for substrate specificity for glucose, maltose as well as other sugars. The assay conditions chosen are adapted to ensure that the expected small enhancements brought about e.g., by a single amino acid substitution, can be measured. This has been accomplished by adjusting the assay conditions such that the wild type (or parent) enzyme activity is close to the lower detection limit. One mode of selection or screening of appropriate mutants is given in Example 3. Any change or improvement as compared over the wild-type enzyme this way can be clearly detected.

It should, of course, be understood that not all expression vectors and DNA regulatory sequences would function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

The invention also relates to a process for producing s-GDH variants of the current invention comprising culturing a host cell of the invention under conditions suitable for production of the mutant s-GDH of the invention. For bacterial host cells, typical culture conditions are liquid medium containing the appropriate antibiotic and induction agent. Typical appropriate antibiotics include ampicillin, canamycin, chloroamphenicol, tetracyclin and the like. Typical induction agents include IPTG, glucose, lactose and the like.

It is preferred that the polypeptides of the present invention are obtained by production in host cells expressing a DNA sequence coding the mutant s-GDH. The polypeptides of the present invention may also be obtained by in vitro translation of the mRNA encoded by a DNA sequence coding for the mutant s-GDH. For example, the DNA sequences may be synthesized as described above and inserted into a suitable expression vector, which in turn may be used in an in vitro transcription/translation system.

An expression vector comprising an isolated polynucleotide as defined and described above operably linked to a promoter sequence capable of promoting its expression in a cell-free peptide synthesis system represents another preferred embodiment of the present invention.

The polypeptides produced e.g. by procedures as describe above, may then be isolated and purified using various routine protein purification techniques. For example, chromatographic procedures such as ion exchange chromatography, gel filtration chromatography and affinity chromatography may be employed.

One of the major applications of the improved s-GDH variants of this invention is for the use in test strips to monitor blood-glucose level in diabetic patients. Due to the insensitivity of PQQ-dependent glucose dehydrogenase towards oxygen, a system using the improved s-GDH variants is less prone to interference by oxygen than systems based on glucose oxidase. More important, since the s-GDH variants have improved specificity towards glucose and significantly decreased relative enzymatic activity towards other sugars, the interference due maltose, galactose, and/or other related sugars which may be present in a sample to be analyzed is significantly reduced. Of course many kinds of samples may be investigated. Bodily fluids like serum, plasma, intestinal fluid or urine are preferred sources for such samples.

The invention also comprises a method of detecting, determining or measuring glucose in a sample using a s-GDH mutant according to the present invention. It is especially preferred that the improved method for detection of glucose in a sample is characterized in that said detection, determination or measurement of glucose is performed using a sensor or test strip device.

Also within the scope of the present invention is a device for the detection or measurement of glucose in a sample comprising a s-GDH mutant according to this invention as well as other reagents required for said measurement.

The s-GDH variants with improved substrate specificity of this invention can also be used to great advantage in biosensors (D'Costa, E. J., et al., Biosensors 2 (1986) 71-87; Laurinavicius, V., et al., Analytical Letters 32 (1999) 299-316; Laurinavicius, V., et al., Monatshefte fuer Chemie 130 (1999) 1269-1281) for online monitoring of glucose in a sample or a reactor. For this purpose, the s-GDH variants can, for example, be used to coat an oxygen-insensitive glassy electrode with an osmium complex containing a redox conductive epoxy network (Ye et al., 1993, supra) for more accurate determination of the glucose concentration.

There are also other possible applications of the s-GDH variants with the improved substrate specificity according to this invention. For example, these s-GDH variants may be used in an aldonic acid production process. Wild-type s-GDH has a high turnover in substrate oxidation producing gluconic and other aldonic acids. By using the s-GDH variants, which are more specific for glucose, the production of gluconic acid would result in much less byproducts. With other s-GDH variants of different substrate specificity, it is possible to produce different aldonic acids as required.

In the following examples, all reagents, restriction enzymes, and other materials were obtained from Roche Diagnostics Germany, unless other commercial sources are specified, and used according to the instructions given by the suppliers. Operations and methods employed for the purification, characterization and cloning of DNA are well known in the art (Ausubel, F., et al., in "Current protocols in molecular biology" (1994), Wiley Verlag) and can be adapted as required by the skilled artisan.

The following examples further illustrate the present invention. These examples are not intended to limit the scope of the present invention, but provide further understanding of the invention.

EXAMPLE 1

Cloning and Expression of the Wild-type *A. calcoaceticus* Soluble PQQ Dependent Glucose Dehydrogenase in *E. coli*

The s-GDH gene was isolated from *Acinetobacter calcoaceticus* strain LMD 79.41 according to standard procedures. The wild-type s-GDH gene was subcloned into a plasmid containing the mgl promoter for adjustabel expression (cf. Patent application WO 88/09373). The new construct was called pACSGDH (see FIGS. 3 and 4). The recombinant plasmids was introduced into a host organism selected from the *E. coli* group. These organisms were then cultivated under appropriate conditions and colonies showing s-GDH activity selected.

The plasmid pACSGDH was isolated from a 200 ml overnight culture of the clone mentioned above using the QIAGEN Plasmid Maxi Kit (Qiagen) according to the manufacturers protocol. The plasmid was resuspended in 1 ml bidest. water. The concentration of the plasmid was determined using a Beckman DU 7400 Photometer. The yield was 600 µg. Then the quality of the plasmid was determined by agarose gel electrophoresis.

EXAMPLE 2

Mutagenic PCR

To generate random mutations in the s-GDH-gene, mutagenic PCR (polymerase chain reaction) was performed. The pACSGDH plasmid and the DNA sequence encoding the mutated enzymes (PCR product from mutagenic PCR) were digested with the restriction enzymes Sph I and Eco RI. The products were gel purified. The digested DNA sequences were ligated and an aliquot of the ligation reaction mixture was used to transform competent *E. coli* cells. The transformants were subsequently selected on LB plates containing ampicillin.

To assay, individual colonies were chosen, grown over night in LB medium containing ampicillin and subjected to screening (see Example 3).

Mutagenic PCR reaction mixture:
40 ng pACSGDH
1× buffer without MgCl2 (Roche Diagnostics GmbH, Cat. 1699 105)
dCTP, dTTP 1 mM
dATP, dGTP 0.2 mM (Roche Diagnostics GmbH, Cat. 1969 064)
40 pmol GF23-Primer (5'-CGC GCA CGC GCA TGC CGC CGA TGT TC) (=SEQ ID NO: 4)
40 pmol GR23 (5'-GAC GGC CAG TGA ATT CTT TCA) (=SEQ ID NO: 5)
7 mM MgCl2
0.6 mM MnCl2
5 U Taq DNA polymerase (Roche Diagnostics GmbH, Cat. 1146 165)
Gene Amp PCR System 2400 (Perkin Elmer), 30 cycles: 95° C. 1 min, 45° C. 2 min, 72° C. 2 min Purification of the PCR products using the High Pure PCR Product Purification Kit from Roche Diagnostics GmbH (Cat. 1 732 676) according to the manufacturers protocol Digestion of the PCR-fragments with 25 U SphI (Roche Diagnostics GmbH, Cat. 606 120) in 1× buffer H (Roche Diagnostics GmbH, Cat. 1 417 991) at 37° C. over night; addition of 25 U EcoRI (Roche Diagnostics GmbH, Cat. 703 737) and further digestion for 3.5 hours Digestion of 50 µg pACSGDH with 180 U SphI and 180 U EcoRI in 1× buffer H for 4 hours at 37° C.

Gel electrophoresis of the digested pACSGDH and the digested fragments using agarose gels (0.8%)

Extraction of the DNA molecules using QIAquick Gel Extraction Kit (Qiagen, Cat. 28706) according to the manufacturers protocol Determination of the concentration of the fragments and the digested vector using a Beckman DU 7400 Photometer Determination of the quality of the purified products by agarose gel electrophoresis Ligation of 100 ng digested vector with 140 ng mPCR-fragments using 1 U T4-DNA-Ligase (Roche Diagnostics GmbH, Cat. 481 220) in a volume of 20 µl at 16° C. over night Electroporation of electrocompetent XL1F-cells (Stratagene) with 1 µl of the ligation reaction with 2.5 KV in 0.2 cm cuvettes using a BioRad E. coli Pulser (BioRad)

After growth in 1 ml LB at 37° C. for one hour, bacteria were plated on LB-Ampicillin Agar plates (100 µg/ml Ampicillin) and grown over night at 37° C.

50% of these clones expressing mutated s-GDH were active using the following screening method.

EXAMPLE 3

Screening

The mutant colonies on agar plates described above where picked in microtiter plates (mtp) containing 200 µl LB-Ampicillin-media/well and incubated over night at 37° C. These plates are called master plates.

From each master plate, 5 µl sample/well was transferred to a mtp containing 5 µl per/well of B (B=Bacterial Protein Extraction Reagent; Pierce No. 78248) for cell disruption and 240 µl of 0.0556 mM pyrollo-quinoline quinone(PQQ); 50 mM Hepes; 15 mM CaCl2 pH 7.0/well for activation of s-GDH were added. To complete the formation of the holoenzyme, the mtp was incubated at 25° C. for 2 hours and at 10° C. over night. This plate is called working plate.

From the working plate 2×10 µl sample/hole were transferred to two empty mtps. After that, one was tested with glucose and the other with maltose or other selected sugar molecules as a substrate. All sugar molecules were used in equimolar concentrations.

The dE/min was calculated and the value using glucose as substrate was set to 100% activity. The value obtained with the other sugar was compared to the glucose value and calculated in percent activity ((dE/min Maltose/dE Glucose) *100). This is equivalent to the cross-reactivity of the (mutant) enzyme.

EXAMPLE 4

Sequencing of Mutant s-GDH Gene from Mutagenic PCR

The plasmid containing the mutant s-GDH gene that leads to 50% maltose/glucose activity was isolated (High Pure Plasmid Isolation Kit, Roche Diagnostics GmbH, No. 1754785) and sequenced using an ABI Prism Dye Terminator Sequencing Kit and ABI 3/73 and 3/77 sequencer (Amersham Pharmacia Biotech).

Following primers were used:

```
Sense strand:
GDH F2:        5'-TTA ACG TGC TGA ACA GCC GG-3'
               (= SEQ ID NO: 6)

GDH F3:        5'-GAT GCT GAT GGG CAG AAT GG-3'
               (= SEQ ID NO: 7)

GDH F4:        5'-ATA TGG GTA AAG TAC TAC GC -3'
               (= SEQ ID NO: 8)

GDH F5:        5'-ACG ATC CAA CTT GTG GAG AG-3'
               (= SEQ ID NO: 9)

Antisense strand:
GDH R1:        5'-CGA TTA AGT TGG GTA ACG CC-3'
               (= SEQ ID NO: 10)

GDH R2:        5'-ATA CGG AAA ATG ACA CCA CG-3'
               (= SEQ ID NO: 11)

GDH R3:        5'-GGG CCT TGT TCA GAC TGC AA-3'
               (= SEQ ID NO: 12)

GDH R4:        5'-CAA GAC GAC CTG ACT GAT GG-3'
               (= SEQ ID NO: 13)

GDH R5:        5'-CAT AAC AAC GCG TGC GGC TT-3'
               (= SEQ ID NO: 14)
```

Results:
=>6 mutations on DNA sequence level
=>4 mutations on amino acid level:
at position 340 (mature enzyme) change from E to G
at position 348 (mature enzyme) change from T to S
at position 369 (mature enzyme) change from N to H
at position 413 (mature enzyme) change from S to N

EXAMPLE 5 s-GDH Mutants Obtained by Saturation Mutagenesis

The QuickChange Site-Directed Mutagenesis Kit (Stratagene, Cat. 200518) was used to substitute successively wild type amino acids at defined positions of the s-GDH-protein or of s-GDH-mutants (plasmide purification as discribed above) with other random amino acids.

The 5'- and the 3'-primer used for mutagenesis were complementary to each other and contained NNN in a central position. These nucleotides were flanked by 12 to 16 nucleotides at each end. The sequences of the nucleotides were identical to the cDNA-strand or to the complementary cDNA-strand flanking the codon for the amino acid that had to be substituted. Instead of the codon, the primer contained NNN therefore the oligonucleotides code for every codon.

For every defined position, one PCR reaction was performed.

The PCR-reactions and the DpnI digestions were performed according to the manual.

After that, 1 μl of each reaction was used for the electroporation of XL1F-cells. Cells were grown and the s-GDH activity of the clones was determined as described above.

To ensure statistically that all 20 amino acids variants were screened, 200 clones were tested for each position.

The following primers where used:

```
for position 340    EGF 5'-TCC AAC TTG TGG ANN
Sense strand            NAT GAC CTA CAT TT-3'
                        (= SEQ ID NO: 15)

Antisense strand    EGR 5'-AAA TGT AGG TCA TNN
                        NTC CAC AAG TTG GA-3'
                        (= SEQ ID NO: 16)

for position 348    TSF 5'-CAT TTG CTG GCC ANN
Sense strand            NGT TGC ACC GTC AT-3'
                        (= SEQ ID NO: 17)

Antisense strand    TSR 5'-ATG ACG GTG CAA CNN
                        NTG GCC AGC AAA TG-3'
                        (= SEQ ID NO: 18)

for position 369    NHF 5'-TAC TGG TTG GGA ANN
Sense strand            NAC ATT ATT GGT TC-3'
                        (= SEQ ID NO: 19)

Antisense strand    NHR 5'-GAA CCA ATA ATG TNN
                        NTT CCC AAC CAG TA-3'
                        (= SEQ ID NO: 20)

for position 413    SNF 5'-TGA TGT GAT TGC ANN
Sense strand            NCC AGA TGG GAA TG-3'
                        (= SEQ ID NO: 21)

Antisense strand    SNR 5'-CAT TCC CAT CTG GNN
                        NTG CAA TCA CAT CA-3'
                        (= SEQ ID NO: 22)
```

Results:

The amino acid changes at positions 340, 369 and 413 didn't change the substrate specificity. Only the wobble at position 348 did yield clones with a substrate specificity from 25-100% (maltose/glucose).

Numerous rounds of mutagenic PCR and saturation mutagenesis were performed. It was found and confirmed that positions 348 and 428 are of major importance and that exchange of other amino acids may further improve the specificity for glucose of mutated s-GDH. Representative data and positions are given in table 1.

TABLE 1

Examples for s-GDH-variants with improved specificity for glucose

| Changed amino acid to wildtype sequence | Glucose conversion | Maltose conversion | Galactose conversion | SA |
|---|---|---|---|---|
| wild-type | 100% | 105% | 50% | 1000 |
| 340 E to G | 100% | 50% | 25% | 700 |
| 348 T to S | | | | |
| 369 N to H | | | | |

TABLE 1-continued

Examples for s-GDH-variants with improved specificity for glucose

| Changed amino acid to wildtype sequence | Glucose conversion | Maltose conversion | Galactose conversion | SA |
|---|---|---|---|---|
| 413 S to N | | | | |
| 22 I to L | 100% | 123% | 14% | 178 |
| 295 Q to L | | | | |
| 422 L to I | | | | |
| 348 T to D | 100% | 80% | n.t. | n.t. |
| 348 T to A | 100% | 67% | n.t. | n.t. |
| 348 T to G | 100% | 22% | 20% | 910 |
| 428 N to P | 100% | 8% | 25% | n.t. |
| 348 T to G | | | | |
| 428 N to V | 100% | 22% | 22% | n.t. |
| 348 T to G | | | | |
| 127 T to M | 100% | 1% | 32% | n.t. |
| 143 D to Q | | | | |
| 348 T to G | | | | |
| 428 N to P | | | | |
| 76 Q to A | 100% | 17% | n.t. | n.t. |
| 348 T to G | | | | |
| 76 Q to M | 100% | 18% | n.t. | n.t. |
| 348 T to G | | | | |
| 76 Q to D | 100% | 17% | n.t. | n.t. |
| 348 T to G | | | | |
| 76 Q to P | 100% | 17% | n.t. | n.t. |
| 348 T to G | | | | |
| 76 Q to S | 100% | 17% | n.t. | n.t. |
| 348 T to G | | | | |
| 76 Q to G | 100% | 20% | n.t. | n.t. |
| 348 T to G | | | | |
| 76 Q to E | 100% | 17% | n.t. | n.t. |
| 348 T to G | | | | |
| 143 D to E | 100% | 17% | n.t. | n.t. |
| 348 T to G | | | | |
| 171 Y to H | 100% | 19% | n.t. | n.t. |
| 348 T to G | | | | |
| 308 K to N | | | | |
| 171 Y to D | 100% | 18% | n.t. | n.t. |
| 348 T to G | | | | |
| 317 F to V | | | | |
| 127 T to S | 100% | 11% | n.t. | n.t. |
| 169 L to H | | | | |
| 348 T to G | | | | |
| 355 Y to H | | | | |
| 16 N to D | 100% | 22% | n.t. | n.t. |
| 120 T to S | | | | |
| 177 Q to R | | | | |
| 277 Y to H | | | | |
| 348 T to G | | | | |
| 116 I to T | 100% | 20% | n.t. | n.t. |
| 255 N to T | | | | |
| 299 K to R | | | | |
| 348 T to G | | | | |
| 227 H to Y | 100% | 18% | n.t. | n.t. |
| 348 T to G | | | | |
| 438 N to S | | | | |
| 341 M to V | 100% | 20% | n.t. | n.t. |
| 348 T to G | | | | |
| 348 T to G | 100% | 10% | n.t. | n.t. |
| 349 V to G | | | | |
| 428 N to P | | | | |
| 171 Y to G | 100% | 3% | n.t. | n.t. |
| 230 P to H | | | | |
| 348 T to G | | | | |
| 428 N to P | | | | |
| 230 P to H | 100% | 10% | n.t. | 200 |
| 348 T to G | | | | |
| 428 N to P | | | | |
| 227 H to F | 100% | 6% | n.t. | n.t. |
| 230 P to H | | | | |
| 348 T to G | | | | |
| 428 N to P | | | | |
| 143 D to E | 100% | 17% | n.t. | n.t. |
| 348 T to G | | | | |
| 143 D to E | 100% | 1% | 32% | n.t. |
| 348 T to G | | | | |

TABLE 1-continued

Examples for s-GDH-variants with improved specificity for glucose

| Changed amino acid to wildtype sequence | Glucose conversion | Maltose conversion | Galactose conversion | SA |
|---|---|---|---|---|
| 428 N to P | | | | |
| 169 G to X<br>230 P to H<br>348 T to G<br>428 N to P | 100% | 2% | n.t. | n.t. |

Abbreviations:
n.t. = not tested
SA = specific activity (U/mg protein) with glucose as substrate

EXAMPLE 6

Purification of Mutant s-GDH T348G

The grown cells (LB-Amp. 37° C.) were harvested and resuspended in potassium phosphate buffer pH 7.0. Cell disruption was performed by French Press passage (700-900 bar). After centrifugation the supernatant was applied to a S-Sepharose (Amersham Pharmacia Biotec) column equilibrated with 10 mM potassium phosphate buffer pH 7.0. After washing, the s-GDH was eluted using a salt gradient 0-1 M NaCl. The fractions showing s-GDH activity were pooled, dialysed against potassium phosphate buffer pH 7.0 and re-chromatographied on re-equilibrated S-sepharose column. The active fractions were pooled and subjected to a gel filtration using a Superdex® 200 column (Amersham Pharmacia Biotec). The active fractions were pooled and stored at −20° C.

Enzyme Assay and Protein Determination of Mutant T348G and Wildtype s-GDH

Protein determination was performed using the Protein Assay Reagent no. 23225 from Pierce (calibration curve with BSA, 30 Min. 37° C.).

The GDH samples were diluted to 1 mg protein/ml with 0.0556 mM pyrollo-quinoline quinone(PQQ); 50 mM Hepes; 15 mM CaCl2 pH 7.0 and incubated at 25° C. for 30 minutes for reconstitution or activation.

After activation 50 µl of sample were added to 1000 µl of a 0.2 M citrate buffer solution (pH 5.8; at 25° C.) containing 0.315 mg (4-(dimethylphosphinylmethyl)-2-methyl-pyrazolo-[1.5a]-imidazol-3-yl)-(4-nitrosophenyl)-amine (see U.S. Pat. No. 5,484,708)/ml as a mediator and 33 mM sugar).

Extinction at 620 nm is monitored during the first 5 minutes at 25° C.

One Unit enzyme activity corresponds the conversion of 1 mMol mediator/min under the above assay conditions Calculation: Activity=(total volume*dE/min [U/ml]):
(ε*sample volume*1)

(ε=coefficient of extinction; in this example $\epsilon_{620\,nm}=30[l*mmol^{-1}*cm^{-1}]$).

The assay was performed with glucose, maltose and galactose (Merck, Germany).

Results:

| Sample | Specific activity U/mg Protein (glucose as substrate) | % maltose/ glucose conversion | % galactose/ glucose conversion |
|---|---|---|---|
| wilde-type | 1000 | 105% | 50% |
| Mutant T348G | 910 | 22% | 20% |

EXAMPLE 7

Determination of Glucose in the Presence or Absence of Maltose

The wild-type and mutant T348G of s-GDH were applied for glucose determination. The reference samples contained 65 mg glucose/dl. The "test"-sample contained 65 mg glucose/dl and 130 mg/dl maltose. The same amounts of GDH activity (U/ml; see enzyme assay) were used for each assay.

In a cuvette was mixed:
1 ml 0.315 mg (4-(dimethylphosphinylmethyl)-2-methyl-pyrazolo-[1.5a]-imidazol-3-yl)-(4-nitrosophenyl)-amine ml/0.2 M citrate pH 5.8
0.015 ml sample (glucose or glucose+maltose)

The assay was started adding 0.050 ml 90 U/ml s-GDH. The change of absorption at 620 nm was monitored. After 5 minutes constant values were observed and the dE/5 min calculated. The value obtained measuring the reference sample with wild-type s-GDH was set to 100%. The other values were compared to this reference value and calculated in %.

Results:

| | 65 mg/dl glucose | 65 mg/dl glucose and 130 mg/dl maltose |
|---|---|---|
| wild-type s-GDH | 100% | 190% |
| mutant s-GDH T348G | 100% | 130% |

It can be clearly seen that the "glucose-value" measured is markedly less impaired when the mutated s-GDH is used in this determination.

List of References

Anthony C., 1996. Quinoprotein-catalysed reactions. Biochem. J. 320(3):697-711

Anthony C., Ghosh M., 1997. The structure and function of PQQ-containing quinoproteins. Curr. Sci. 72(10): 716-727

Anthony, C., Biochem J 320 (1996) 697-711

Anthony, C. and Ghosh, M., Current Science 72 (1997) 716-727

Anthony, C. and Ghosh, M., Prog Biophys Mol Biol 69 (1998) 1-21

Anthony, C., Biochem Soc Trans 26 (1998) 413-7

Ausubel, F., et al., in "Current protocols in molcular biology" (1994), Wiley Verlag Cleton-Jansen, A. M., et al., Antonie Van Leeuwenhoek 56 (1989) 73-9

Cleton-Jansen, A. M., et al., J Bacteriol 170 (1988) 2121-5

Cleton-Jansen, A. M., et al., Mol Gen Genet 217 (1989) 430-6

Davidson, V. L. in "Principles and applications of quinoproteins" (1993) the whole book, New York, Marcel Dekker D'Costa, E. J., et al., Biosensors 2 (1986) 71-87

Dokter, P., et al., FEMS Microbiology Letters 43 (1987) 195-200
Dokter, P., et al., Biochem J 239 (1986) 163-7
Dokter, P., et al., Biochem J 254 (1988) 131-8
Duine, J. A. Energy generation and the glucose dehydrogenase pathway in *Acinetobacter* in "The Biology of *Acinetobacter*" (1991) 295-312, New York, Plenum Press
Duine, J. A., Biosens. Bioelectronics 10 (1995) 17-23
Duine, J. A., et al., Arch Microbiol 131 (1982) 27-31
Duine, J. A., Eur J Biochem 200 (1991) 271-84
Goodwin, P. M. and Anthony, C., Adv Microb Physiol 40 (1998) 1-80
Hill, D. E., et al., Methods Enzymol 155 (1987) 558-68
Igarashi, S., et al., Biochem Biophys Res Commun 264 (1999) 820-4
Kaufmann, N., et al. Development and evaluation of a new system for determining glucose from fresh capillary blood and heparinised venous blood in "Glucotrend" (1997) 1-16,
Mannheim, Boehringer Mannheim GmbH
Laurinavicius, V., et al., Analytical Letters 32 (1999) 299-316
Laurinavicius, V., et al., Monatshefte fuer Chemie 130 (1999) 1269-1281
Leung, D. W., et al., Technique 1 (1989) 11-15
Matsushita, K. and Adachi, O. Bacterial quinoproteins glucose dehydrogenase and alcohol dehydrogenase in "Principles and applications of Quinoproteins" (1993) 47-63, New York, Marcel Dekker
Matsushita, K., et al., Antonie Van Leeuwenhoek 56 (1989) 63-72
Matsushita, K., et al., Biochemistry 28 (1989) 6276-80
Matsushita, K., et al., Bioscience Biotechnology & Biochemistry 59 (1995) 1548-1555
Oliphant, A. R., et al., Gene 44 (1986) 177-83
Olsthoorn, A. J. and Duine, J. A., Arch Biochem Biophys 336 (1996) 42-8
Olsthoorn, A. J. and Duine, J. A., Biochemistry 37 (1998) 13854-61
Oubrie, A. and Dijkstra, B. W., Protein Sci 9 (2000) 1265-73
Oubrie, A., et al., Embo J 18 (1999) 5187-94
Oubrie, A., et al., J Mol Biol 289 (1999) 319-33
Oubrie, A., et al., Proc Natl Acad Sci USA 96 (1999) 11787-91
Sambrook, J., et al.—in "Molecular Cloning: A Laboratory Manual" (1989)—, Cold Spring Harbour, N.Y., Cold Spring Harbour Laboratory Press
Wens, R., et al., Perit Dial Int 18 (1998) 603-9
Ye, L., et al., Anal. Chem. 65 (1993) 238-41
EP 0 620 283
JP 11243949
U.S. Pat. No. 5,484,708
U.S. Pat. No. 5,997,817
U.S. Pat. No. 6,057,120
U.S. Pat. No. 6,103,509
WO 92/07953
WO 99/30152
WO 88/09373

The invention claimed is:

1. A pyrroloquinoline quinone (PQQ)-dependent soluble glucose dehydrogenase (s-GDH) mutant, comprising an amino acid sequence that is at least 90% identical to SEQ ID NO: 24 and wherein said mutant comprises an alanine or a serine substitution for threonine at position 348 of SEQ ID NO: 24 and wherein the mutant has s-GDH activity.

2. The mutant of claim 1, wherein at least one amino acid residue selected from the group consisting of $Gln_{76}$, $Asp_{143}$, $Gln_{168}$, $Leu_{169}$, and $Asn_{428}$, of SEQ ID NO: 24, is substituted with another amino acid.

3. The mutant of claim 1, wherein the glutamine at position 76 of SEQ ID NO: 24 is substituted with a different amino acid.

4. The mutant of claim 1 wherein the asparagine at position 428 of SEQ ID NO: 24 is substituted with another amino acid.

5. The mutant of claim 4, wherein at least one amino acid residue selected from the group consisting of $Gln_{76}$, $Thr_{127}$, and $Asp_{143}$, of SEQ ID NO: 24, is substituted with a different amino acid.

6. The mutant of claim 4, wherein at least one amino acid residue selected from the group consisting of $Glu_{245}$ and $Met_{341}$, of SEQ ID NO: 24, is substituted with a different amino acid.

7. The mutant of claim 3, wherein the glutamine at position 76, of SEQ ID NO: 24, is substituted with an amino acid selected from the group consisting of alanine, methionine, aspartic acid, proline, serine, glycine, and glutamic acid.

8. The mutant of claim 1 wherein amino acid residues other than glutamine and asparagine are present at positions 76 and 428, respectively, of SEQ ID NO: 24.

9. A PQQ-dependent s-GDH mutant, said mutant comprising an amino acid sequence at least 90% identical to SEQ ID NO: 24 wherein said mutant comprises a serine substitution for threonine at position 348 of SEQ ID NO: 24 and wherein the mutant has s-GDH activity.

10. A PQQ-dependent s-GDH mutant, said mutant comprising an amino acid sequence at least 90% identical to SEQ ID NO: 24 wherein said mutant comprises an alanine substitution for threonine at position 348 of SEQ ID NO: 24 and wherein the mutant has s-GDH activity.

11. The mutant of claim 1 further wherein tyrosine, glycine, and serine residues are substituted at positions 227, 348, and 438, respectively, of SEQ ID NO: 24.

* * * * *

```
                         SEQUENCE LISTING

<160> NUMBER OF SEQ ID NOS: 25

<210> SEQ ID NO 1
<211> LENGTH: 7
<212> TYPE: PRT
<213> ORGANISM: Acinetobacter calcoaceticus
<220> FEATURE:
<221> NAME/KEY: MISC_FEATURE
<222> LOCATION: (3)..(3)
<223> OTHER INFORMATION: any amino acid other than Thr

<400> SEQUENCE: 1

Trp Pro Xaa Val Ala Pro Ser
 1               5

<210> SEQ ID NO 2
<211> LENGTH: 7
<212> TYPE: PRT
<213> ORGANISM: Acinetobacter calcoaceticus
<220> FEATURE:
<221> NAME/KEY: MISC_FEATURE
<222> LOCATION: (4)..(4)
<223> OTHER INFORMATION: any amino acid other than Asn

<400> SEQUENCE: 2

Thr Ala Gly Xaa Val Gln Lys
 1               5

<210> SEQ ID NO 3
<211> LENGTH: 7
<212> TYPE: PRT
<213> ORGANISM: Acinetobacter calcoaceticus
<220> FEATURE:
<221> NAME/KEY: MISC_FEATURE
<222> LOCATION: (4)..(4)
```

<223> OTHER INFORMATION: any amino acid

<400> SEQUENCE: 3

Ala Asp Gly Xaa Asn Gly Leu
 1               5

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
      sense primer GF23

<400> SEQUENCE: 4
cgcgcacgcg catgccgccg atgttc                                          26

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      antisense primer GR23

<400> SEQUENCE: 5
gacggccagt gaattctttt cta                                             23

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      sense primer GDH F2

<400> SEQUENCE: 6
ttaacgtgct gaacagccgg                                                 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      sense primer GDH F3

<400> SEQUENCE: 7
gatgctgatg ggcagaatgg                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      sense primer GDH F4

<400> SEQUENCE: 8
atatgggtaa agtactacgc                                                 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic sense primer GDH F5

<400> SEQUENCE: 9
acgatccaac ttgtggagag                                                    20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense primer GDH R1

<400> SEQUENCE: 10
cgattaagtt gggtaacgcc                                                    20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense primer GDH R2

<400> SEQUENCE: 11
atacggaaaa tgacaccacg                                                    20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense primer GDH R3

<400> SEQUENCE: 12
gggccttgtt cagactgcaa                                                    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense primer GDH R4

<400> SEQUENCE: 13
caagacgacc tgactgatgg                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      antisense primer GDH R5

<400> SEQUENCE: 14
cataacaacg cgtgcggctt                                                    20

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      sense primer EGF

```
<220> FEATURE:
<221> NAME/KEY: MISC_FEATURE
<222> LOCATION: (14)..(16)
<223> OTHER INFORMATION: a, c, g, t, unknown or other

<400> SEQUENCE: 15
tccaacttgt ggannnatga cctacattt                                29

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      antisense primer EGR
<220> FEATURE:
<221> NAME/KEY: MISC_FEATURE
<222> LOCATION: (14)..(16)
<223> OTHER INFORMATION: a, c, g, t, unknown or other

<400> SEQUENCE: 16
aaatgtaggt catnnntcca caagttgga                                29

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      sense primer TSF
<220> FEATURE:
<221> NAME/KEY: MISC_FEATURE
<222> LOCATION: (14)..(16)
<223> OTHER INFORMATION: a, c, g, t, unknown or other

<400> SEQUENCE: 17
catttgctgg ccannngttg caccgtcat                                29

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: Synthetic
      antisense primer TSR
<220> FEATURE:
<221> NAME/KEY: MISC_FEATURE
<222> LOCATION: (14)..(16)
<223> OTHER INFORMATION: a, c, g, t, unknown or other

<400> SEQUENCE: 18
atgacggtgc aacnnntggc cagcaaatg                                29

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      sense primer NHF
<220> FEATURE:
<221> NAME/KEY: MISC_FEATURE
<222> LOCATION: (14)..(16)
<223> OTHER INFORMATION: a, c, g, t, unknown or other

<400> SEQUENCE: 19
tactggttgg gaannnacat tattggttc                                29

<210> SEQ ID NO 20
```

-continued

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      antisense primer NHR
<220> FEATURE:
<221> NAME/KEY: MISC_FEATURE
<222> LOCATION: (14)..(16)
<223> OTHER INFORMATION: a, c, g, t, unknown or other

<400> SEQUENCE: 20
gaaccaataa tgtnnnttcc caaccagta                                   29

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      sense primer SNF
<220> FEATURE:
<221> NAME/KEY: MISC_FEATURE
<222> LOCATION: (14)..(16)
<223> OTHER INFORMATION: a, c, g, t, unknown or other

<400> SEQUENCE: 21
tgatgtgatt gcannnccag atgggaatg                                   29

<210> SEQ ID NO 22
<211> LENGTH: 29
<212> TYPE: DNA
<213> ORGANISM: Artificial Sequence
<220> FEATURE:
<223> OTHER INFORMATION: Description of Artificial Sequence: Synthetic
      antisense primer SNR
<220> FEATURE:
<221> NAME/KEY: MISC_FEATURE
<222> LOCATION: (14)..(16)
<223> OTHER INFORMATION: a, c, g, t, unknown or other

<400> SEQUENCE: 22
cattcccatc tggnnntgca atcacatca                                   29

<210> SEQ ID NO 23
<211> LENGTH: 1362
<212> TYPE: DNA
<213> ORGANISM: Acinetobacter calcoaceticus
<220> FEATURE:
<221> NAME/KEY: CDS
<222> LOCATION: (1)..(1362)

<400> SEQUENCE: 23

```
gat gtt cct cta act cca tct caa ttt gct aaa gcg aaa tca gag aac      48
Asp Val Pro Leu Thr Pro Ser Gln Phe Ala Lys Ala Lys Ser Glu Asn
 1               5                  10                  15 ttt gac aag aaa gtt att cta tct aat cta aat aag ccg cac gcg ttg      96
Phe Asp Lys Lys Val Ile Leu Ser Asn Leu Asn Lys Pro His Ala Leu
                20                  25                  30 tta tgg gga cca gat aat caa att tgg tta act gag cga gca aca ggt     144
Leu Trp Gly Pro Asp Asn Gln Ile Trp Leu Thr Glu Arg Ala Thr Gly
            35                  40                  45 aag att cta aga gtt aat cca gag tcg ggt agt gta aaa aca gtt ttt     192
Lys Ile Leu Arg Val Asn Pro Glu Ser Gly Ser Val Lys Thr Val Phe
        50                  55                  60 cag gta cca gag att gtc aat gat gct gat ggg cag aat ggt tta tta     240
Gln Val Pro Glu Ile Val Asn Asp Ala Asp Gly Gln Asn Gly Leu Leu
    65                  70                  75                  80
```

-continued

| | |
|---|---|
| ggt ttt gcc ttc cat cct gat ttt aaa aat aat cct tat atc tat att<br>Gly Phe Ala Phe His Pro Asp Phe Lys Asn Asn Pro Tyr Ile Tyr Ile<br>                85                    90                 95 | 288 |
| tca ggt aca ttt aaa aat ccg aaa tct aca gat aaa gaa tta ccg aac<br>Ser Gly Thr Phe Lys Asn Pro Lys Ser Thr Asp Lys Glu Leu Pro Asn<br>        100                   105                110 | 336 |
| caa acg att att cgt cgt tat acc tat aat aaa tca aca gat acg ctc<br>Gln Thr Ile Ile Arg Arg Tyr Thr Tyr Asn Lys Ser Thr Asp Thr Leu<br>            115                   120             125 | 384 |
| gag aag cca gtc gat tta tta gca gga tta cct tca tca aaa gac cat<br>Glu Lys Pro Val Asp Leu Leu Ala Gly Leu Pro Ser Ser Lys Asp His<br>130                   135                 140 | 432 |
| cag tca ggt cgt ctt gtc att ggg cca gat caa aag att tat tat acg<br>Gln Ser Gly Arg Leu Val Ile Gly Pro Asp Gln Lys Ile Tyr Tyr Thr<br>145                     150                 155             160 | 480 |
| att ggt gac caa ggg cgt aac cag ctt gct tat ttg ttc ttg cca aat<br>Ile Gly Asp Gln Gly Arg Asn Gln Leu Ala Tyr Leu Phe Leu Pro Asn<br>                   165                 170             175 | 528 |
| caa gca caa cat acg cca act caa caa gaa ctg aat ggt aaa gac tat<br>Gln Ala Gln His Thr Pro Thr Gln Gln Glu Leu Asn Gly Lys Asp Tyr<br>            180                   185             190 | 576 |
| cac acc tat atg ggt aaa gta cta cgc tta aat ctt gat gga agt att<br>His Thr Tyr Met Gly Lys Val Leu Arg Leu Asn Leu Asp Gly Ser Ile<br>               195                 200             205 | 624 |
| cca aag gat aat cca agt ttt aac ggg gtg gtt agc cat att tat aca<br>Pro Lys Asp Asn Pro Ser Phe Asn Gly Val Val Ser His Ile Tyr Thr<br>210                   215                 220 | 672 |
| ctt gga cat cgt aat ccg cag ggc tta gca ttc act cca aat ggt aaa<br>Leu Gly His Arg Asn Pro Gln Gly Leu Ala Phe Thr Pro Asn Gly Lys<br>225                     230                 235             240 | 720 |
| tta ttg cag tct gaa caa ggc cca aac tct gac gat gaa att aac ctc<br>Leu Leu Gln Ser Glu Gln Gly Pro Asn Ser Asp Asp Glu Ile Asn Leu<br>            245                   250             255 | 768 |
| att gtc aaa ggt ggc aat tat ggt tgg cca aat gta gca ggt tat aaa<br>Ile Val Lys Gly Gly Asn Tyr Gly Trp Pro Asn Val Ala Gly Tyr Lys<br>               260                 265             270 | 816 |
| gat gat agt ggc tat gct tat gca aat tat tca gca gca gcc aat aag<br>Asp Asp Ser Gly Tyr Ala Tyr Ala Asn Tyr Ser Ala Ala Ala Asn Lys<br>            275                   280             285 | 864 |
| tca att aag gat tta gct caa aat gga gta aaa gta gcc gca ggg gtc<br>Ser Ile Lys Asp Leu Ala Gln Asn Gly Val Lys Val Ala Ala Gly Val<br>        290                   295                300 | 912 |
| cct gtg acg aaa gaa tct gaa tgg act ggt aaa aac ttt gtc cca cca<br>Pro Val Thr Lys Glu Ser Glu Trp Thr Gly Lys Asn Phe Val Pro Pro<br>305                     310                 315             320 | 960 |
| tta aaa act tta tat acc gtt caa gat acc tac aac tat aac gat cca<br>Leu Lys Thr Leu Tyr Thr Val Gln Asp Thr Tyr Asn Tyr Asn Asp Pro<br>                   325                   330             335 | 1008 |
| act tgt gga gag atg acc tac att tgc tgg cca aca gtt gca ccg tca<br>Thr Cys Gly Glu Met Thr Tyr Ile Cys Trp Pro Thr Val Ala Pro Ser<br>               340                 345             350 | 1056 |
| tct gcc tat gtc tat aag ggc ggt aaa aaa gca att act ggt tgg gaa<br>Ser Ala Tyr Val Tyr Lys Gly Gly Lys Lys Ala Ile Thr Gly Trp Glu<br>            355                   360             365 | 1104 |
| aat aca tta ttg gtt cca tct tta aaa cgt ggt gtc att ttc cgt att<br>Asn Thr Leu Leu Val Pro Ser Leu Lys Arg Gly Val Ile Phe Arg Ile<br>370                   375                 380 | 1152 |
| aag tta gat cca act tat agc act act tat gat gac gct gta ccg atg<br>Lys Leu Asp Pro Thr Tyr Ser Thr Thr Tyr Asp Asp Ala Val Pro Met | 1200 |

```
                385                 390                 395                 400
ttt aag agc aac aac cgt tat cgt gat gtg att gca agt cca gat ggg         1248
Phe Lys Ser Asn Asn Arg Tyr Arg Asp Val Ile Ala Ser Pro Asp Gly
                    405                 410                 415 aat gtc tta tat gta tta act gat act gcc gga aat gtc caa aaa gat         1296
Asn Val Leu Tyr Val Leu Thr Asp Thr Ala Gly Asn Val Gln Lys Asp
        420                 425                 430 gat ggc tca gta aca aat aca tta gaa aac cca gga tct ctc att aag         1344
Asp Gly Ser Val Thr Asn Thr Leu Glu Asn Pro Gly Ser Leu Ile Lys
            435                 440                 445 ttc acc tat aag gct aag                                                 1362
Phe Thr Tyr Lys Ala Lys
    450

<210> SEQ ID NO 24
<211> LENGTH: 454
<212> TYPE: PRT
<213> ORGANISM: Acinetobacter calcoaceticus

<400> SEQUENCE: 24

Asp Val Pro Leu Thr Pro Ser Gln Phe Ala Lys Ala Lys Ser Glu Asn
 1               5                  10                  15

Phe Asp Lys Lys Val Ile Leu Ser Asn Leu Asn Lys Pro His Ala Leu
                20                  25                  30

Leu Trp Gly Pro Asp Asn Gln Ile Trp Leu Thr Glu Arg Ala Thr Gly
            35                  40                  45

Lys Ile Leu Arg Val Asn Pro Glu Ser Gly Ser Val Lys Thr Val Phe
        50                  55                  60

Gln Val Pro Glu Ile Val Asn Asp Ala Asp Gly Gln Asn Gly Leu Leu
 65                  70                  75                  80

Gly Phe Ala Phe His Pro Asp Phe Lys Asn Asn Pro Tyr Ile Tyr Ile
                    85                  90                  95

Ser Gly Thr Phe Lys Asn Pro Lys Ser Thr Asp Lys Glu Leu Pro Asn
                100                 105                 110

Gln Thr Ile Ile Arg Arg Tyr Thr Tyr Asn Lys Ser Thr Asp Thr Leu
            115                 120                 125

Glu Lys Pro Val Asp Leu Leu Ala Gly Leu Pro Ser Ser Lys Asp His
        130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Asn Gly Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Val Ser His Ile Tyr Thr
        210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Asp Glu Ile Asn Leu
                245                 250                 255

Ile Val Lys Gly Gly Asn Tyr Gly Trp Pro Asn Val Ala Gly Tyr Lys
            260                 265                 270

Asp Asp Ser Gly Tyr Ala Tyr Ala Asn Tyr Ser Ala Ala Ala Asn Lys
        275                 280                 285
```

```
Ser Ile Lys Asp Leu Ala Gln Asn Gly Val Lys Val Ala Ala Gly Val
    290                 295                 300

Pro Val Thr Lys Glu Ser Glu Trp Thr Gly Lys Asn Phe Val Pro Pro
305                 310                 315                 320

Leu Lys Thr Leu Tyr Thr Val Gln Asp Thr Tyr Asn Tyr Asn Asp Pro
                325                 330                 335

Thr Cys Gly Glu Met Thr Tyr Ile Cys Trp Pro Thr Val Ala Pro Ser
            340                 345                 350

Ser Ala Tyr Val Tyr Lys Gly Lys Lys Ala Ile Thr Gly Trp Glu
        355                 360                 365

Asn Thr Leu Leu Val Pro Ser Leu Lys Arg Gly Val Ile Phe Arg Ile
    370                 375                 380

Lys Leu Asp Pro Thr Tyr Ser Thr Thr Tyr Asp Ala Val Pro Met
385                 390                 395                 400

Phe Lys Ser Asn Asn Arg Tyr Arg Asp Val Ile Ala Ser Pro Asp Gly
                405                 410                 415

Asn Val Leu Tyr Val Leu Thr Asp Thr Ala Gly Asn Val Gln Lys Asp
            420                 425                 430

Asp Gly Ser Val Thr Asn Thr Leu Glu Asn Pro Gly Ser Leu Ile Lys
        435                 440                 445

Phe Thr Tyr Lys Ala Lys
    450

<210> SEQ ID NO 25
<211> LENGTH: 4373
<212> TYPE: DNA
<213> ORGANISM: Artificial Sequence
<220> FEATURE:
<223> OTHER INFORMATION: Description of Artificial Sequence: vector
      pACSGDH

<400> SEQUENCE: 25
cactaactga ttacgcaccg catgtaaccg ttttcaatct gtgagtaaat tcacagttta      60
ttaacattgt gatagctatg atgacaacgt tgtcgcact gtaactaacg tgtaacagtt     120
agttgtcagt tttgctgggg tatttcgctt ataaaaccg ttatcacaat atcccgcgac     180
taccggacaa aaataaagag ttgaataaga gcttatccca ttagggctat tttacttgcc     240
attttggacc tgggcagtgc tcgccaaaac gcgttagcgt tttgaacgcg ctagcggcgg     300
cccgaagggc gagcgtagcg agtcaaacct cacgtactac gtgtacgctc cggttttgc      360 gcgctgtccg tgtccaaact gctgcgccaa taacgcctgg tgggatagg  tctaaatacg     420 cttcggcgtt cagtaacacg cgttaacgtg ctgaacagcc gggcattttt ttacgctata     480
ccctacataa taaaaccgga gctaccatga ataagaaggt actgaccctt tctgccgtga     540
tggcaagtct gttattcggc gcgcacgcgc atgccgccga tgttcctcta actccatctc     600
aatttgctaa agcgaaatca gagaactttg acaagaaagt tattctatct aatctaaata     660
agccgcacgc gttgttatgg ggaccagata atcaaatttg gttaactgag cgagcaacag     720
gtaagattct aagagttaat ccagagtcgg gtagtgtaaa acagttttt caggtaccag      780 agattgtcaa tgatgctgat gggcagaatg gtttattagg ttttgccttc catcctgatt     840
ttaaaaataa tccttatatc tatatttcag gtacatttaa aaatccgaaa tctacagata     900
aagaattacc gaaccaaacg attattcgtc gttataccta taataaatca acagatacgc     960
tcgagaagcc agtcgattta ttagcaggat taccttcatc aaaagaccat cagtcaggtc    1020
```

-continued

```
gtcttgtcat tgggccagat caaaagattt attatacgat tggtgaccaa gggcgtaacc     1080
agcttgctta tttgttcttg ccaaatcaag cacaacatac gccaactcaa caagaactga     1140
atggtaaaga ctatcacacc tatatgggta aagtactacg cttaaatctt gatgaagta      1200 ttccaaagga taatccaagt tttaacgggg tggttagcca tatttataca cttggacatc     1260
gtaatccgca gggcttagca ttcactccaa atggtaaatt attgcagtct gaacaaggcc     1320
caaactctga cgatgaaatt aacctcattg tcaaaggtgg caattatggt tggccgaatg     1380
tagcaggtta taaagatgat agtggctatg cttatgcaaa ttattcagca gcagccaata     1440
agtcaattaa ggatttagct caaaatggag taaaagtagc cgcaggggtc cctgtgacga     1500
aagaatctga atggactggt aaaaactttg tcccaccatt aaaaacttta tataccgttc     1560
aagataccta caactataac gatccaactt gtggagagat gacctacatt tgctggccaa     1620
cagttgcacc gtcatctgcc tatgtctata agggcggtaa aaaagcaatt actggttggg     1680
aaaatacatt attggttcca tctttaaaac gtggtgtcat tttccgtatt aagttagatc     1740
caacttatag cactacttat gatgacgctg taccgatgtt aagagcaac aaccgttatc      1800 gtgatgtgat tgcaagtcca gatgggaatg tcttatatgt attaactgat actgccggaa     1860
atgtccaaaa agatgatggc tcagtaacaa atacattaga aaacccagga tctctcatta     1920
agttcaccta taaggctaag taatacagtc gcattaaaaa accgatctat aaagatcggt     1980
ttttttagtt ttagaaaaga attcactggc cgtcgtttta caacgtcgtg actgggaaaa     2040
ccctggcgtt acccaactta atcgccttgc agcacatccc cctttcgcca gctggcgtaa     2100
tagcgaagag gcccgcaccg atcgcccttc ccaacagttg cgcagcctga atggcgaatg     2160
gcgcctgatg cggtattttc tccttacgca tctgtgcggt atttcacacc gcatatggtg     2220
cactctcagt acaatctgct ctgatgccgc atagttaagc cagccccgac acccgccaac     2280
acccgctgac gcgccctgac gggcttgtct gctcccggca tccgcttaca gacaagctgt     2340
gaccgtctcc gggagctgca tgtgtcagag gttttcaccg tcatcaccga aacgcgcgag     2400 acgaaaggc ctcgtgatac gcctatttt ataggttaat gtcatgataa taatggtttc       2460
ttagacgtca ggtggcactt ttcggggaaa tgtgcgcgga accctatttt gttattttt      2520 ctaaatacat tcaaatatgt atccgctcat gagacaataa ccctgataaa tgcttcaata     2580
atattgaaaa aggaagagta tgagtattca acatttccgt gtcgccctta ttcccttttt     2640
tgcggcattt tgccttcctg tttttgctca cccagaaacg ctggtgaaag taaaagatgc     2700
tgaagatcag ttgggtgcac gagtgggtta catcgaactg gatctcaaca gcggtaagat     2760
ccttgagagt tttcgccccg aagaacgttt tccaatgatg agcactttta agttctgct      2820 atgtggcgcg gtattatccc gtattgacgc cgggcaagag caactcggtc gccgcataca     2880
ctattctcag aatgacttgg ttgagtactc accagtcaca gaaaagcatc ttacggatgg     2940
catgacagta agagaattat gcagtgctgc cataaccatg agtgataaca ctgcggccaa     3000
cttacttctg acaacgatcg gaggaccgaa ggagctaacc gcttttttgc acaacatggg     3060
ggatcatgta actcgccttg atcgttggga accggagctg aatgaagcca taccaaacga     3120
cgagcgtgac accacgatgc ctgtagcaat ggcaacaacg ttgcgcaaac tattaactgg     3180
cgaactactt actctagctt cccggcaaca attaatagac tggatggagg cggataaagt     3240
tgcaggacca cttctgcgct cggcccttcc ggctggctgg tttattgctg ataaatctgg     3300
agccggtgag cgtgggtctc gcggtatcat tgcagcactg gggccagatg gtaagccctc     3360
ccgtatcgta gttatctaca cgacggggag tcaggcaact atggatgaac gaaatagaca     3420
```

```
gatcgctgag ataggtgcct cactgattaa gcattggtaa ctgtcagacc aagtttactc    3480
atatatactt tagattgatt taaaacttca tttttaattt aaaaggatct aggtgaagat    3540
cctttttgat aatctcatga ccaaaatccc ttaacgtgag ttttcgttcc actgagcgtc    3600 agacccgta  gaaaagatca aaggatcttc ttgagatcct ttttttctgc gcgtaatctg    3660
ctgcttgcaa acaaaaaaac caccgctacc agcggtggtt tgtttgccgg atcaagagct    3720
accaactctt tttccgaagg taactggctt cagcagagcg cagataccaa atactgtcct    3780
tctagtgtag ccgtagttag gccaccactt caagaactct gtagcaccgc ctacatacct    3840
cgctctgcta atcctgttac cagtggctgc tgccagtggc gataagtcgt gtcttaccgg    3900
gttggactca agacgatagt taccggataa ggcgcagcgg tcgggctgaa cggggggttc    3960
gtgcacacag cccagcttgg agcgaacgac ctacaccgaa ctgagatacc tacagcgtga    4020
gctatgagaa agcgccacgc ttcccgaagg gagaaaggcg gacaggtatc cggtaagcgg    4080
cagggtcgga acaggagagc gcacgaggga gcttccaggg ggaaacgcct ggtatcttta    4140
tagtcctgtc gggtttcgcc acctctgact tgagcgtcga ttttttgtgat gctcgtcagg    4200 ggggcggagc ctatggaaaa acgccagcaa cgcggccttt ttacggttcc tggccttttg    4260
ctggcctttt gctcacatgt tctttcctgc gttatcccct gattctgtgg ataaccgtat    4320
taccgccttt gagtgagctg ataccgctcg ccgcagccga acgacggggc ccg           4373
```